(12) United States Patent
Kietzmann et al.

(10) Patent No.: US 8,921,080 B2
(45) Date of Patent: Dec. 30, 2014

(54) PIG LIVER ESTERASES

(75) Inventors: Martin Kietzmann, Graz (AT); Harald Pichler, Deutschlandsberg (AT); Helmut Schwab, Graz (AT); Amin El-Heliebi, Graz (AT); Christine Winkler, Graz (AT); Andreas Braun, Graz (AT)

(73) Assignee: DSM IP Assets B.V., Heerlen (NL)

( * ) Notice: Subject to any disclaimer, the term of this patent is extended or adjusted under 35 U.S.C. 154(b) by 148 days.

(21) Appl. No.: 13/265,178

(22) PCT Filed: Apr. 26, 2010

(86) PCT No.: PCT/EP2010/055564
§ 371 (c)(1),
(2), (4) Date: Dec. 30, 2011

(87) PCT Pub. No.: WO2010/122175
PCT Pub. Date: Oct. 28, 2010

(65) Prior Publication Data
US 2012/0100582 A1 Apr. 26, 2012

(30) Foreign Application Priority Data
Apr. 24, 2009 (EP) .................................. 09158759

(51) Int. Cl.
*C12N 9/18* (2006.01)
(52) U.S. Cl.
CPC ....................................... *C12N 9/18* (2013.01)
USPC .......... 435/132; 536/23.2; 435/197; 435/136; 435/155; 435/135; 435/280
(58) Field of Classification Search
CPC ........................................................ C12N 9/18
See application file for complete search history.

(56) References Cited

FOREIGN PATENT DOCUMENTS

| WO | WO 02/48322 | 6/2002 |
|---|---|---|
| WO | WO 2004/055177 | 7/2004 |
| WO | WO 2007/073845 | 7/2007 |
| WO | WO 2008/116745 | 10/2008 |
| WO | WO 2009/004093 | 1/2009 |

OTHER PUBLICATIONS

International Search Report for PCT/EP2010/055564, mailed Jun. 18, 2010.
Hermann et al., "Alternative pig liver esterase (APLE)—Cloning, identification and functional expression in *Pichia pastoris* of a versatile new biocatalyst", *Journal of Biotechnology*, vol. 133, No. 9, Nov. 2007, pp. 301-310.
Musidlowska-Persson et al., "Recombinant porcine intestinal carboxylesterase: cloning from the pig liver esterase gene by site-directed mutagenesis, functional expression and characterization", *Protein Engineering*, vol. 16, No. 12, Dec. 2003, pp. 1139-1145.

*Primary Examiner* — Rebecca Prouty
(74) *Attorney, Agent, or Firm* — Nixon & Vanderhye P.C.

(57) ABSTRACT

The invention relates to an isolated polypeptide having esterase activity comprising an amino acid sequence shown in any one of SEQ ID NO's 2, 4, 6, 8, 10, 12 or 14 or a homologue thereof, comprising an amino acid substitution or deletion of one or more amino acids as shown in said SEQ ID NO's and resulting in a mutant polypeptide having an increased concentration of the fraction of the mutant polypeptide being present as an active and soluble protein in cleared lysate of the mutant polypeptide expressed in *E. coli* relative to the concentration of the fraction of the polypeptide without the mutation being present as an active and soluble protein in cleared lysate of the polypeptide without the one or more deletion or substitution expressed in *E. coli* under the same conditions. The invention also relates to nucleic acid encoding the polypeptides according to the invention, and the use of the polypeptides.

13 Claims, 6 Drawing Sheets

PIG LIVER ESTERASES

This application is the U.S. national phase of International Application No. PCT/EP2010/055564 filed 26 Apr. 2010 which designated the U.S. and claims priority to EP Patent Application No. 09158759.2 filed 24 Apr. 2009, the entire contents of each of which are hereby incorporated by reference.

The invention relates to isolated mutant polypeptides having esterase activity and having an increased concentration of the fraction of the polypeptide being present as an active and soluble protein in cleared lysate of the polypeptide expressed in E. coli relative to the polypeptide without certain mutations in its amino acid sequence. The invention also relates to isolated nucleic acid sequences encoding the mutant pig liver esterases and to use of the mutant polypeptides according to the invention.

Pig liver esterases (PLEs) are known as a very useful class of hydrolases, for example they are very useful in the enantioselective hydrolysis of esters. The fact that they are deemed useful is quite astonishing as there have been severe drawbacks for the use of PLEs, a crude lysate isolated from pig liver. (i) There are various iso-enzymes having different properties and enantioselectivity can, therefore, change from batch to batch and can also change with reaction time due to differences in operational stability. (ii) The risk of viral or prion contamination of crude pig liver extract is a major concern for the pharmaceutical industry. (iii) In addition, products made with the help of PLEs might not be considered kosher or halal.

Because of these limitations, various efforts are known to recombinantly produce pig liver iso-enzymes. While initially the methylotrophic yeast *Pichia pastoris* seemed to be a good expression system for pig liver esterases, in the end *Escherichia coli* proved to be a better host after improvement of specific host, gene and expression systems contributing to correct enzyme folding.

International patent application WO 2009/004093 describes the expression of pig liver esterase in *E. coli*, and is hereby incorporated by reference.

Since PLEs are such useful enzymes, there remains a need to further improve the activity levels that can be achieved with the enzyme.

Surprisingly, it has now been found that expression levels and therefore activity levels of pig liver esterase iso-form mutants and homologous esterases expressed in *E. coli* can significantly be improved by substituting one or more residues in its amino acid sequence, namely one or more of the amino acids responsible for multimer formation of the pig liver esterase, by an amino acid that does not result in or reduces the tendency for multimer formation, thereby changing the quaternary structure of PLE.

The finding was triggered by the preparation of a mutation on position 788 of the Open Reading Frame encoding APLE (SEQ ID NO 1), which is corresponding to nucleotide position 5541 in SEQ ID NO 1, whereby the replacement was T->A, leading to the replacement of the hydrophobic valine in the APLE enzyme by a negatively charged aspartic acid: V263D. A computer model indicated that this mutation was located on a helix at the very outside of the enzyme, thus, remote from the active site cavity of the enzyme, while it was also found that the total activity of this mutated enzyme towards (4E)-5-chloro-2-isopropylpent-4-enoic-acid methyl ester increased from 6.5 to 11.6 Units/mg total soluble protein. In case of dimethyl-3-(3,4-dichlorphenyl)-glutarate, activity increased from 36 to 42 mU/mg of total soluble protein and in case of para-nitrophenyl acetate activity raised from 15.4 to 24.3 U/mg total soluble protein. At first, there was no explanation why a mutation in an outer region of APLE would have such a strong effect on various conversions. However, analysis of the structure of the human homolog hCE1 identified valine on position 263 of APLE as being potentially important for multimerization. Upon introducing a charged aspartic acid instead, the formerly existing hydrophobic interaction, stabilizing interaction between two subunits, is impaired. A negatively charged amino acid may repel the other subunit instead of binding it through hydrophobic interaction.

Next, the hypothesis of multimer formation being disrupted by a change introduced by aspartic acid on position 263 disrupting hydrophobic interactions and, therefore, leading to the formation of monomers was tested. Analyzing a computer model of APLE it was concluded that valine on position 263 of one monomer may interact with leucine on position 43 of another monomer. It was postulated that trimer formation is at least partly due to alternating hydrophobic interaction of L43 and V263 between three sub-units in total. Thus, regardless of which amino acid is replaced by aspartic acid the interaction should be interrupted. Testing the hypothesis, leucine on position 43 was replaced by aspartic acid, which resulted in monomerisation.

This mutation also resulted in monomer formation, thus, this proved that the replacement of amino acids at certain positions of a PLE monomer that without the replacement can form a multimer increases the amount of enzyme present in the monomeric form, and although the L43D variant yielded less soluble protein than the V263D variant, it is clear that the activity found for a certain amount of cleared lysate comprising enzymes mutated at a position involved in multimer formation and used for a certain conversion increased relative to the same amount of cleared lysate comprising enzymes without mutations used for the same conversion. The same mutation was introduced in all polypeptides according to any one of SEQ ID NO's 2, 4, 6, 8, 10, 12 or 14, and resulted in the same effect.

Thus, the invention relates to an isolated polypeptide having esterase activity comprising an amino acid sequence shown in any one of SEQ ID NO's 2, 4, 6, 8, 10, 12 or 14 or a homologue thereof, comprising an amino acid substitution or deletion of one or more amino acids as shown in said SEQ ID NO's and resulting in a mutant polypeptide having an increased concentration of the fraction of the mutant polypeptide being present as an active and soluble protein in cleared lysate of the mutant polypeptide expressed in *E. coli* relative to the concentration of the fraction of the polypeptide without the mutation being present as an active and soluble protein in cleared lysate of the polypeptide without the one or more deletion or substitution expressed in *E. coli* under the same conditions.

It is preferred to substitute one or more of the amino acids rather than to delete one or more amino acids.

In this text, relative esterase activity is a comparison of activities of wild-type (i.e. the non mutagenized parent enzyme) and the respective mutant enzyme which were prepared (see at the Materials and methods section under the header "Expression and cell harvest"; where preparation of cleared lysate is described and where under "Quantification of PLE activity" the methods for measuring activity are described) under the same conditions using the same amount of the soluble protein preparation (cleared lysate). The relative activity (r [%]) is calculated by the release of para-nitrophenol per minute of the mutant lysate ([p-NPAmut]) divided by the release of para-nitrophenol per minute of the corresponding wild-type lysate ([p-NPAwt]) multiplied by 100% according to the formula r=([p-NPAmut]/[p-NPAwt])×100%.

In one embodiment, the invention relates to an isolated polypeptide according to the invention, which polypeptide shows an increase of 10% in esterase activity compared to the esterase activity of the corresponding wild-type polypeptide without deletion or substitution of amino acids.

Enzymes have a primary (amino acid sequence), secondary (mainly alpha-helix and beta-sheet) and tertiary (structure of one peptide chain) structure. In addition, some enzymes form quaternary structures which are conglomerates (multimers) of the same (homo) or different (hetero) subunits (peptide chains). Pig liver esterases are homo trimers. The quaternary structure of the enzymes and mutants can be tested by glycerol density gradient centrifugation (see Example 3 for a description of Glycerol density gradient centrifugation) and native gel electrophoresis (see in the Materials and Methods section under the header "Native Gel Electrophoresis" for a description of the method).

Multimer formation is usually caused by multiple intermolecular attractive forces of different amino acids such as hydrophobic/hydrophobic or ionic (positive/negative) interactions of the different subunits (monomers). Such interactions are often stabilizing enzymes and are, therefore, often beneficial for enzymes. In the present invention it was surprisingly found that destruction of only a few of such attractive forces lead to a changed quaternary structure and higher relative activities of PLE and homologous enzymes in cleared lysates.

Thus, the invention relates to an isolated polypeptide having esterase activity comprising an amino acid sequence shown in any one of SEQ ID NO's 2, 4, 6, 8, 10, 12 or 14 or a homologue thereof, comprising an amino acid substitution or deletion of one or more amino acids as shown in said SEQ ID NO's, wherein at least one amino acid substitution or deletion has taken place at an amino acid position which is located at a point of interaction of monomers when the monomers are forming multimers and which destroys that point of interaction between the monomers, and resulting in a mutant polypeptide having an increased concentration of the fraction of the mutant polypeptide being present as an active and soluble protein in cleared lysate of the mutant polypeptide expressed in E. coli relative to the concentration of the fraction of the polypeptide without the mutation being present as an active and soluble protein in cleared lysate of the polypeptide without the one or more deletion or substitution expressed in E. coli under the same conditions. Preferably, the invention relates to an isolated polypeptide having esterase activity comprising an amino acid sequence according to any one of SEQ ID NO's 2, 4, 6, 8, 10, 12 or 14, and isolated polypeptides having an amino acid identity of at least more than 90%, preferably more than 95% identity to any one of SEQ ID NO's 2, 4, 6, 8, 10, 12 or 14, and where at least one amino acid substitution or deletion has taken place at an amino acid position which is located at a point of interaction of monomers when the monomers are forming multimers and which destroys that point of interaction between the monomers. Preferably the substitution or deletion has been carried out at one or more positions selected from the group of amino acid positions 43, 260, 263, 266 or 270, or positions corresponding thereto. Preferred substitutions are L43D, T260P, T260A, V263D and V263G or positions corresponding thereto.

In particular, the invention relates to isolated polypeptides having esterase activity said polypeptide comprising an amino acid sequence shown in any one of SEQ ID NO's 2, 4, 6, 8, 10, 12 or 14 or a homologue thereof having an amino acid identity of more than 90%, preferably more than 95%, more preferably more than 97%, most preferably more than 98% identity to any one of SEQ ID NO's 2, 4, 6, 8, 10, 12 or 14, comprising one or more amino acid substitutions selected from the group of positions 43, 260, 263 or positions corresponding thereto, preferably those substitutions are selected from the group of substititions L43D, T260P, T260A, V263D, V263G or positions corresponding thereto.

In the framework of this invention percentages identity (or homology) were or may be determined as described in Tatiana A. Tatusova, Thomas L. Madden (1999), "Blast 2 sequences—a new tool for comparing protein and nucleotide sequences", FEMS Microbiol Lett. 174:247-250, using the following standard parameters at http://vvww.ncbi.nlm.nih.gov/BLAST/bl2seq/wblast2.cgi for Protein sequences:
Matrix: BLOSUM62
Open gap: 5
extension gap: 2
Penalties gap x_dropoff: 11
Expected: 10
word size: 11
for nucleotides:
Reward for match:1
Penalty for mismatch:-2
Open gap: 11
extension gap: 1
Penalties gap x_dropoff: 50
Expected: 10
word size: 3

Positions that can be targeted for destroying attractive forces of different monomers can be identified by analyzing X-ray structures of PLE or homologous enzymes (e.g. human liver carboxylesterase 1, PDB entry 1MX1 or the rabbit liver carboxylesterase 1, PDB entry 1K4Y) or by random mutagenesis experiments. Preferred amino acid positions for targeting substitutions are positions 43, 260 and 263, and amino acids of other subunits that interact with these amino acids. After identification of amino acid positions that contribute to the quaternary structure using the known methods, amino acid substitutions are chosen to destroy the attractive forces. Preferred substitutions are exchange of hydrophobic residues, e.g. Alanine (abbreviated as Ala or A), Valine (abbreviated as Val or V), Isoleucine (abbreviated as Ile or I), Leucine (abbreviated as Leu or L), Methionine (abbreviated as Met or M), Phenylalanine (abbreviated as Phe or F), Tryptophane (abbreviated as Trp or W), Cysteine (abbreviated as Cys or C), Proline (abbreviated as Pro or P), with less hydrophobic or hydrophilic amino acids, e.g. Lysine (abbreviated as Lys or K), Arginine (abbreviated as Arg or R), Aspartic acid (abbreviated as Asp or D), Glutamic acid (abbreviated as Glu or E), Serine (abbreviated as Ser or S), Tyrosine (abbreviated as Tyr or Y), Threonine (abbreviated as Thr or T), Glycine (abbreviated as Gly or G), Histidine (abbreviated as His or H), Glutamine (abbreviated as Gln or Q), Asparagine (abbreviated as Asn or N) and vice versa. Other preferred amino acid substitutions target destruction of ionic forces by substituting positively charged amino acids (e.g. Lysine, Arginine or Histidine) with negatively charged amino acids (e.g. Aspartic acid or Glutamic acids) or vice versa.

Thus, a preferred mutation is the replacement of L43 with any amino acid chosen from the group of K, R, D, E, S, Y, T, G, H, Q and N. Another preferred mutation is the replacement of T260 with any amino acid chosen from the group of A, V, I, L, M, F, W, C and P. Another preferred mutation is H266 with any amino acid chosen from the group of A, V, I, L, M, F, W, C and P and D and E. Another preferred mutation is the replacement of Q270 with any amino acid chosen from the group of A, V, I, L, M, F, W, C and P. All mutations are described relative to any one of the amino acid sequences according to SEQ ID NO's 2, 4, 6, 8, 10, 12 or 14.

Particularly preferred are the following mutations, based on the amino acid sequence of any one of SEQ ID NO's 2, 4, 6, 8, 10, 12 or 14: V263D, L43D, T260P and T260A.

It will be understood by a person skilled in the art that one or more combinations of the described mutations are also possible, as long as the replacements do not result in an amino acid sequence that allows increased multimer formation relative to the amount of multimer formation before the mutation to occur.

As is known, the numbering of amino acids is dependent on the species the protein originates from. The numbering can also change as the result of deletions or insertions. It is known, however, to a skilled person how to align sequences. Thus, in this text the phrase "or corresponding thereto" is used to describe amino acid positions that except for the number, are the same as the positions 43, 260 and 263 in SEQ ID NO 1.

The isolated polypeptides of the invention may in addition to mutations that decrease multimer formation comprise one or more further mutation, that improve the selectivity and/or activity towards a desired substrate.

Thus, in a preferred embodiment the invention relates to an isolated polypeptide having esterase activity, said polypeptide comprising an amino acid sequence shown in any one of SEQ ID NO's 2, 4, 6, 8, 10, 12 or 14 or a homologue thereof having an amino acid identity of at least more than 90%, preferably more than 95% identity to any one of SEQ ID NO's 2, 4, 6, 8, 10, 12 or 14, comprising one or more amino acid substitutions at positions 43, 260 and 263, or positions corresponding thereto, and one or more amino acid substitution selected from the group of F234S and L238V. Even more preferred in this embodiment, the amino acid substitutions are one or more substitutions on one or more positions selected from the group of position comprising position 43, position 260 and position 263, or more specifically selected from the group of L43D, T260P, T260A, V263D and V263G.

The F234S mutation was the result of the replacement of T on position 701 of the gene encoding for APLE by C. The L238V mutation was the result of the replacement of T by A on position 712 of the gene encoding for APLE. Independent of the mutations that prevent multimer formation, mutants of any one of the polypeptides comprising an amino acid sequence according to any one of SEQ ID NO's 2, 4, 6, 8, 10, 12 or 14 comprising at least one of these two mutations are very useful for the conversion of para-Nitrophenyl acetate, and/or dimethyl-3-(3,4-dichlorphenyl)-glutarate and/or for the resolution of racemic (4e)-5-chloro-2-isopropylpent-4-enoic acid methyl ester. Thus, the invention also relates to such polypeptides.

Thus, the invention also relates to an isolated polypeptide having esterase activity, said polypeptide comprising an amino acid sequence shown in any one of SEQ ID NO's 2, 4, 6, 8, 10, 12 or 14 or a homologue thereof having an amino acid identity of at least 95% identity, preferably 97%, more preferably 98% to any one of SEQ ID's NO's 2, 4, 6, 8, 10, 12 or 14, comprising one or more amino acid substitutions selected from the group of L238V and F234S. Preferably, in addition to the L238V and/or F234S mutation being present, the following positions have the following amino acid residues: at positions 129, 133, 134, 138 and 139 the residues are V, S, T, L and A, respectively. The invention also relates to nucleic acids encoding the polypeptides according to any one of SEQ ID NO's 2, 4, 6, 8, 10, 12 or 14 having at least one mutation chosen from L238V and F234S. Also the use of the polypeptides according to any one of SEQ ID NO's 2, 4, 6, 8, 10, 12 or 14 having at least one mutation chosen from L238V and F234S for the production of an acid, ester or alcohol, or more in particular for the conversion of para-Nitrophenyl acetate, or the resolution of racemic (4e)-5-chloro-2-isopropylpent-4-enoic acid methyl ester or the conversion of dimethyl-3-(3,4-dichlorphenyl)-glutarate is part of the invention.

The invention also relates to nucleic acids encoding the isolated polypeptides according to the invention. In particular, the invention relates to nucleic acids which are the coding sequences in SEQ ID NO's 1, 3, 5, 7, 9, 11 or 13 and homologues thereof, preferably with more than 80% identity, more preferably more than 90%, even more preferred more than 95%, most preferably more than 98% identity to nucleic acids which are the coding sequences in SEQ ID NO's 1, 3, 5, 7, 9, 11 or 13.

In an embodiment, the invention relates to a process for the manufacture of acids, esters or alcohols, wherein an isolated peptide according to the invention is applied. Also, the invention relates to such process wherein α-alkylated acids and/or esters are manufactured, more specifically a process wherein optically pure α-alkylated acids selected from these α-alkylated acids are reduced to their corresponding alcohols. In a further embodiment, these alcohols are further applied as building blocks for dipeptide mimetics, dipeptide mimetics being synthetic copies of natural dipeptides. Furthermore, the invention relates to the application of these building blocks in blood pressure lowering agents.

The invention further relates to all possible combinations of different embodiments and/or preferred features according to the isolated peptide, the nucleic acid sequence, the use of the polypeptide and the process according to the invention as described herein.

In addition, the invention relates to all embodiments in combination with SEQ ID NO's 1, 3, 5, 7, 9, 11 and 13, wherein the polypeptides are encoded by the Open Reading Frames indicated in these sequences.

Materials and Methods

General techniques to prepare polypeptides and mutants thereof are known in the art, and may be found in e.g. Sambrook et al. Molecular Cloning: A Laboratory Manual, 3$^{rd}$ edition, Cold Spring Harbor Laboratory, Cold Spring Harbor, N.Y., (2001).

Preparation of Recombinant *E. Coli* Expressing APLE, γPLE, PICE, PLE2, PLE3, PLE4, PLE5 and Corresponding Mutants.

Synthetic genes γPLE, PICE, PLE2, PLE3, PLE4, PLE5 (see SEQ ID NO's 4, 6, 8, 10, 12 or 14) were cut with NdeI and HindIII and cloned into the NdeI and HindIII restriction sites of pCm470_DsbC_APLE-C8P which is coding for APLE (see SEQ ID NO 2 and FIG. 1) using standard molecular biology techniques as described in Sambrook, J., Fritsch, E. F. and Manniatis, T. (1989). Molecular Cloning: A Laboratory Manual, 2$^{nd}$ ed. Cold Spring Harbor Laboratory Press.

pCm470_DsbC_APLE-C8P and the plasmids derived above coding for APLE, γPLE, PICE, PLE2, PLE3, PLE4, PLE5 were transformed into *E. coli* Origami B (DE3).

Mutants of APLE, γPLE, PICE, PLE2, PLE3, PLE4, PLE5 were prepared by site-saturation mutagenesis using the QuikChange® Site-Directed Mutagenesis Kit (Catalog #200518) of Stratagene (Stratagene, 11011 North Torrey Pines Road La Jolla, Calif. 92037) according to the provided INSTRUCTION MANUAL using the above described plasmids coding for APLE, γPLE, PICE, PLE2, PLE3, PLE4, PLE5 as templates.

Examples for mutagenesis primers for site directed mutagenesis are described in SEQ ID NO's 15-24. The resulting mutant plasmids of APLE, γPLE, PICE, PLE2, PLE3, PLE4, PLE5 were transformed into *E. coli* Origami B (DE3).

```
SeqID 15: Primer L43D_F
5' GTCCCTTTTGCTAAGCCACCTGACGGATCTTTGAGGTTTGC 3'

SeqID 16: Primer L43D_R
5' GCAAACCTCAAAGATCCGTCAGGTGGCTTAGCAAAAGGGAC 3'

SeqID 17: Primer T260P_F
5' GCAGGATGCAAAACTACTCCTTCGGCAGTCTTCGTGC 3'

SeqID 18: Primer T260P_R
5' GCACGAAGACTGCCGAAGGAGTAGTTTTGCATCCTGC 3'

SeqID 19: Primer T260A_F
5' GCAGGATGCAAAACTACTGCTTCGGCAGTCTTCGTGC 3'

SeqID 20: Primer T260A_R
5' GCACGAAGACTGCCGAAGCAGTAGTTTTGCATCCTGC 3'

SeqID 21: Primer V263D_F
5' CTACTACTTCGGCAGACTTCGTGCATTGTTTGC 3'

SeqID 22: Primer V263D_R
5' GCAAACAATGCACGAAGTCTGCCGAAGTAGTAG 3'

SeqID 23: Primer V263G_F
5' CAAAACTACTACTTCGGCAGGGTTCGTGCATTGTTTGCGTC 3'

SeqID 24: Primer V263G_R
5' GACGCAAACAATGCACGAACCCTGCCGAAGTAGTAGTTTTG 3'
```

Expression and Cell Harvest.

All media components and antibiotics were bought from Roth GmbH & Co. KG (Karlsruhe, Germany). Culturing conditions were as follows: 20 ml of pre-culture medium LB medium (Lennox), containing 10 µg/ml chloramphenicol were inoculated with colonies of recombinant *E. coli* expressing APLE, γPLE, PICE, PLE2, PLE3, PLE4, PLE5 and corresponding mutants (preparation see above) and incubated in 100 ml Erlenmeyer flasks at 28° C. and 200 rpm over night (18 h). 10 ml thereof were used to inoculate 500 ml of main culture medium LB medium (Lennox), containing 10 µg/ml chloramphenicol) in 2 l baffled shake flasks. The main culture was incubated at 28° C. and 120 rpm and was induced by 0.1 mM IPTG at $OD_{600}$ 0.6-0.8 over night (18 h). For harvesting cells, cultures were centrifuged at 4,000×g for 10 min at 4° C. Pellets were resuspended in 25 ml 20 mM potassium phosphate buffer, pH 8.0. Cells were sonicated in an ice-water cooled pulping beaker for 5 min with 80% duty cycle and output control level 8 using a Branson Sonfier® 250 (Branson, Danbury, USA). After centrifugation at 75,600×g and 10° C. for 1 h the supernatant containing soluble proteins was sterile filtered (0.2 µm filters) and stored at 4° C. These cleared lysates were used for activity determination using the para-nitrophenyl acetate (p-NPA) (Sigma-Aldrich Laborchemikalien GmbH, Seelze, Germany) assay.

Native Gel Electrophoresis

Blue native gel electrophoresis (BN-PAGE) of bacterial lysates containing APLE was performed according to the method described by Reisinger and Eichacker (2006), "Analysis of membrane protein complexes by blue native PAGE", Proteomics 6 Suppl 2, 6-15, with the following modifications. Aliquots containing 200 µg of soluble proteins were diluted with 10 mM Tris/HCl pH 7.4 to a final volume of 95 µl. Five µl of loading buffer was added to the sample before applying them on an 8-16% linear gradient gel. Gradient gels (16×20 cm) were created with the help of a Bio-Rad Gradient Former model 485 (Bio-Rad Laboratories, Vienna, Austria). Electrophoresis was performed at a constant current of 24 mA per gel at 4° C. After electrophoresis, gels were incubated in 0.1 M potassium phosphate buffer, pH 7.0, for 20 min at room temperature. For the in-gel-detection of esterase activity, the substrate fluorescein diacetate (FDA) was dissolved in acetone [4 mg/ml] and applied on a Biodyne® A membrane (0.45 mm, 16×20 cm) (Pall Life Science, Michigan, USA). After evaporation of acetone, the membrane was brought in close contact with the gel which was placed on a glass plate. The gel-membrane sandwich was incubated at 37° C. for 30 min before detection of fluorescent bands.

SDS-PAGE, Western Blot Analysis and Native Gel Electrophoresis.

SDS-PAGE was based on standard protocols. Prior to loading onto the gels (separation gel: 12.5%, stacking gel: 4%) samples containing 80 µg of total proteins were mixed with respective amount of 2× sample buffer and heated at 40° C. for 15 min. ATE 22 Mighty Small Transphor Tank Transfer Unit (Amersham Biosciences, Uppsala, Sweden) was used for blotting proteins onto a Hybond-ECL™ nitrocellulose membrane (Amersham Biosciences). The primary antibody was a polyclonal rabbit antibody against porcine liver carboxylesterase (abcam, Cambridge, UK). The secondary antibody was a polyclonal goat-anti-rabbit antibody conjugated with alkaline phosphatase adsorbed against human serum proteins (Leinco Technologies, St. Louis, USA). Detection was either done with BCIP/NBT detection (CALBIOCHEM/EMD, La Jolla, USA) directly on the membrane. Protein standard used was PageRuler™ prestained protein ladder (Fermentas GmbH, St. Leon-Rot, Germany).

Quantification of PLE Activity.

Activity towards rac. (4E)-5-chloro-2-isopropylpent-4-enoic-acid methyl ester and dimethyl-3-(3,4-dichlorphenyl)-glutarate was determined by autotitration. Measurements were performed on a Mettler Toledo DL50 GraphiX (Mettler-Toledo GmbH; Giessen, Germany), using 0.1 M and 0.01 M NaOH, respectively, as titrating agent (Roth GmbH & Co. KG, Karlsruhe, Germany). The total reaction mixture of 50 ml consisted of 5 ml substrate i.e. racemic (4E)-5-chloro-2-isopropylpent-4-enoic-acid methyl ester or dimethyl-3-(3,4-dichlorphenyl)-glutarate [100 mg/ml] dissolved in toluene, 5 ml of 10% Tergitol® NP-9 (Sigma-Aldrich, Vienna, Austria) and 10 to 40 mg of soluble proteins. Volumes were adapted to 50 ml by 20 mM potassium phosphate buffer, pH 8.0.

The following p-NPA assay is used:

Para-nitrophenyl acetate (p-NPA) (Sigma-Aldrich Laborchemikalien GmbH, Seelze, Germany) assays were performed with cleared lysates at room temperature in 100 mM Tris/HCl buffer, pH 7.0, using 2 mM p-NPA. The release of para-nitrophenol was quantified at 405 nm ($\epsilon$=9.5946 ml µmol-1 cm-1) using a BeckmanCoulterDU® 800 Spectrophotometer (Beckman Coulter GmbH, Krefeld, Germany). One unit is defined as the amount of enzyme which releases 1 µmol para-nitrophenol in one minute under the above reaction conditions.

EXAMPLES

The invention will be elucidated with reference to the following examples, without however being restricted by these:

Example 1

Quantification of PLE Activity

The p-NPA assay as described above was used as the amount of enzyme which releases 1 µmol para-nitrophenol in one minute under the above reaction conditions.

FIG. 2 shows the increase in total cellular activity towards p-NPA of V263D-mutant PLEs expressed in *E. coli* compared to the PLE wild-type enzymes without the V263D-mutation expressed in *E. coli*. As the 100% level for each PLE is taken the level of the respective PLE wild-type variant.

In the framework of this invention all polypeptides according to any one of SEQ ID NO's 2, 4, 6, 8, 10, 12 or 14 and homologues thereof are referred to as PLE. Thus, also the enzyme called Porcine Intestinal Carboxyl Esterase (PICE) is a PLE in the framework of this invention.

It is clear that all PLE's upon inserting the V263D mutation showed an improved activity.

Example 2

The change in the quarternary structure from multimer to monomer in iso-enzymes with V263D mutations was further seen on native protein gel electrophoresis (FIG. 3).

Esterase activity was visualized herein through staining with fluorescein resulting from hydrolysis of fluorescein diacetate (FDA). All 7 wild-type enzymes are trimers of about the same height on the native gel, whereas the V263D mutants show bands on the lower third of the gel. Multiple bands were excised and analyzed on an SDS-PAGE gel. Multiple bands result in one clear band at the size of about 58 kDa (data not shown). It is assumed that these bands result from different conformations of the same monomer.

Example 3

Determination of Quaternary Structure Glycerol Density Gradient Centrifugation 1 ml fractions ranging from 50% to 5% glycerol in 20 mM potassium phosphate buffer, pH 8.0, were carefully layered on top of each other into Ultra-Clear™ centrifuge tubes (14× 89 mm) (Beckman, Palo Alto, USA). Afterwards, 500 µl lysate containing soluble proteins in the same buffer were carefully layered on top. High speed centrifugation at approx. 200,000×g was performed in a SW 41 rotor (Beckman, Palo Alto, USA) for 20 h at 4° C. Fractions, i.e. 500 µl of 0% glycerol and 1 ml of 5-50% glycerol, were carefully collected in 1.5 ml reaction tubes and stored at 4° C.

Filter Assay:

Whatman Qualitative Standard Filter Circles—Student Grade/Grade 93Ø85 mm (Whatman International Ltd., Maidstone, England) were soaked in assay mix containing 2 mg/ml phenol red, pH 7.5, 1% (v/v) Tergitol® NP-9 (Sigma-Aldrich Laborchemikalien GmbH, Seelze, Germany) and 10% (v/v) racemic (4E)-5-chloro-2-isopropylpent-4-enoic-acid methyl ester (DSM Fine Chemicals Austria GmbH, Linz, Austria) (for the supplemental FIGS. 5-10, the substrate was 10% (v/v) racemic dimethyl methylsuccinate). If the pH value of the assay mix was too low, increasing volumes of 1 M potassium phosphate buffer, pH 8.0, were added. 2 µl of cell free extracts were spotted onto the filters. Color change from red to yellow, caused by hydrolysis of esters and liberation of respective carboxylic acids, indicated enzyme activity. The quality of the substrate, the amount of additional buffer and the starting pH determined the time necessary for a color change.

The result shows that the main fraction of the wild-type APLE localizes between 25% and 30% glycerol concentration, while the main fraction of the mutant, monomeric APLE localizes between 15 and 20% glycerol, see FIG. 4.

Similar experiments were performed for all naturally occurring PLE variants, and they all showed the same effect.

(See supplemental FIGS. 5-10). Protein standard used in all supplemental experiments was the PageRuler™ prestained protein ladder.

Example 4

The activity towards para-nitrophenyl acetate (light grey) and dimethyl-3-(3,4-dichlorphenyl)-glutarate (grey), and the activity towards para-nitrophenyl acetate (light grey) and rac. (4E)-5-chloro-2-isopropylpent-4-enoic-acid methyl ester (dark grey) was measured as described above under "The Materials and methods" section, "Quantification of PLE-activity". The results are shown in FIG. 11a en 11b.

SEQUENCE LISTING

<160> NUMBER OF SEQ ID NOS: 24

Figure 1:
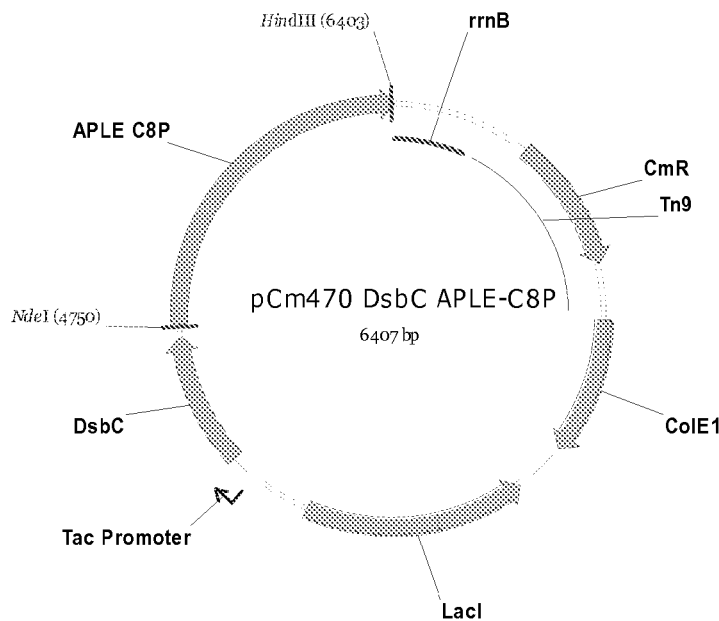
FIG. 1: shows pCm470_DsbC_APLE-C8P.
Figure 2:
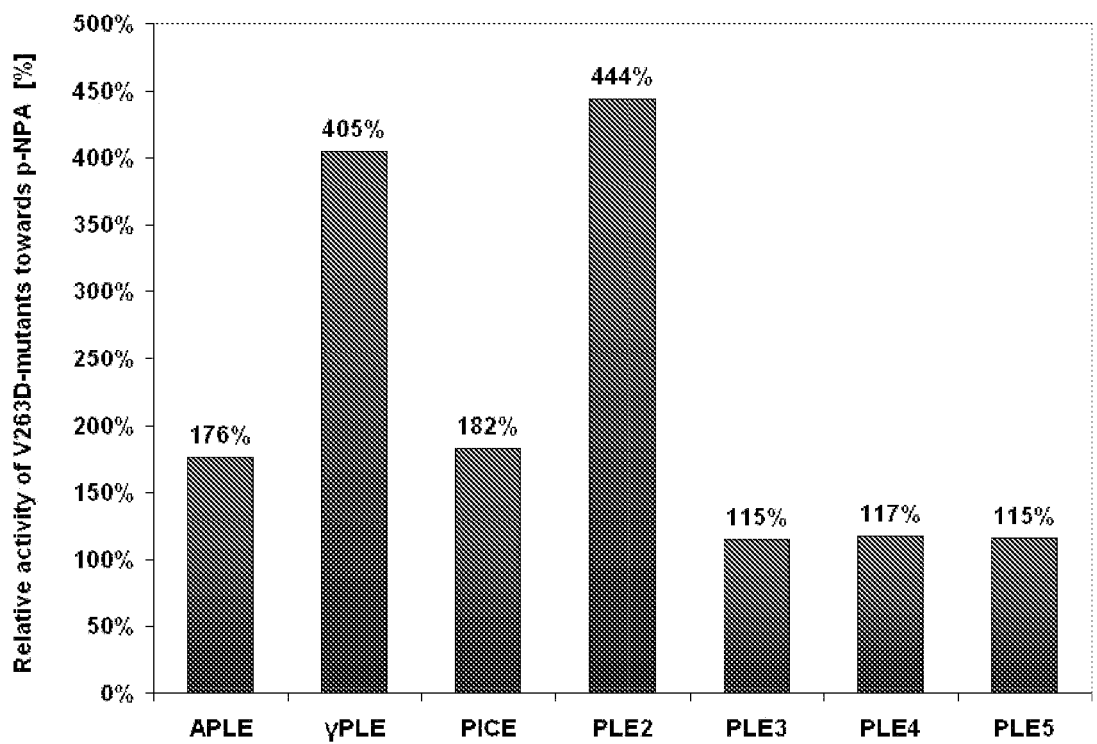
FIG. 2: shows the increase in total cellular activity towards p-NPA of V263D-mutant PLEs expressed in *E. coli* compared to the PLE wild-type enzymes without the V263D-mutation expressed in *E. coli*.
Figure 3:
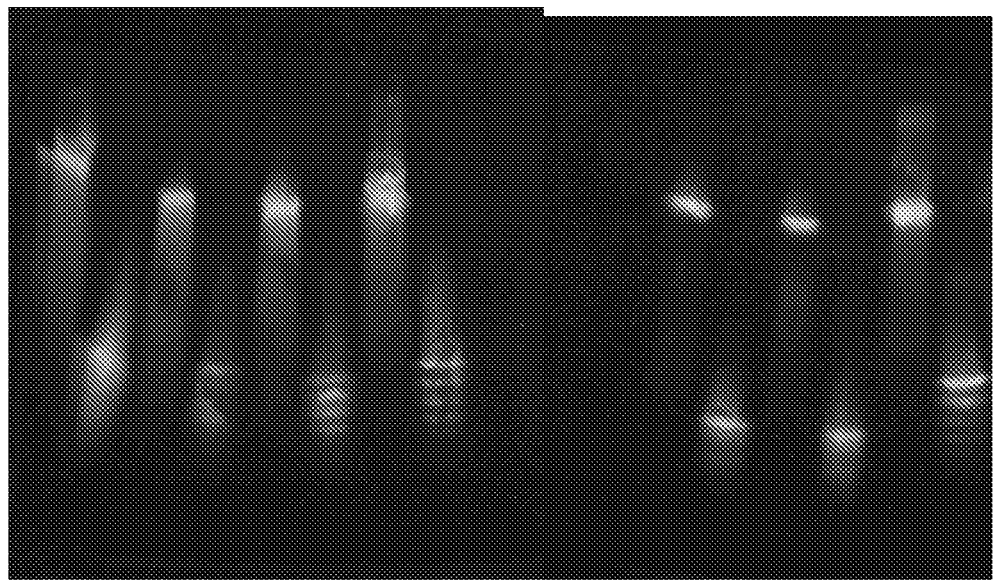
FIG. 3:
1a. APLE
1b: APLE with V263D mutation
2a: PLE3
2b: PLE3 with V263D mutation
3a: PLE4
3b: PLE4 with V263D mutation
4a: PLE5
4b: PLE5 with V263D mutation
Neg.C: negative control *E. coli* origami B
5a: γ-PLE
5b: γ-PLE with V263D mutation
6a: PLE2
6b: PLE2 with V263D mutation
7a: PICE
7b: PICE with V263D mutation
Figure 4:
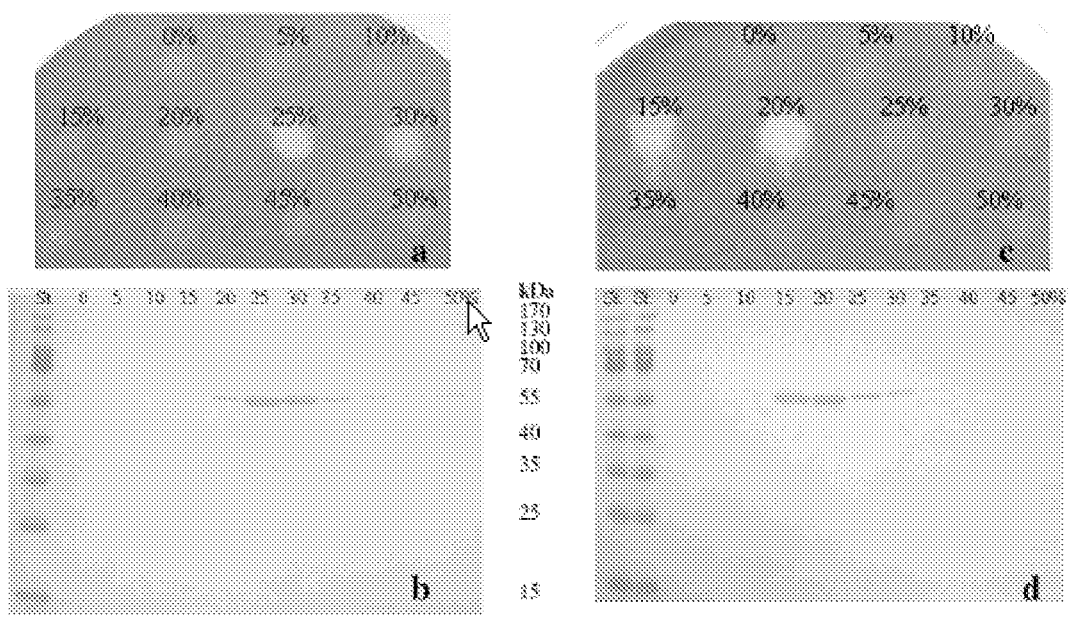
FIG. 4:
a, b: APLE wild-type
c, d: APLE-V263D
a, c: PH-shift assays
b, d: Western Blotting
Figure 5:
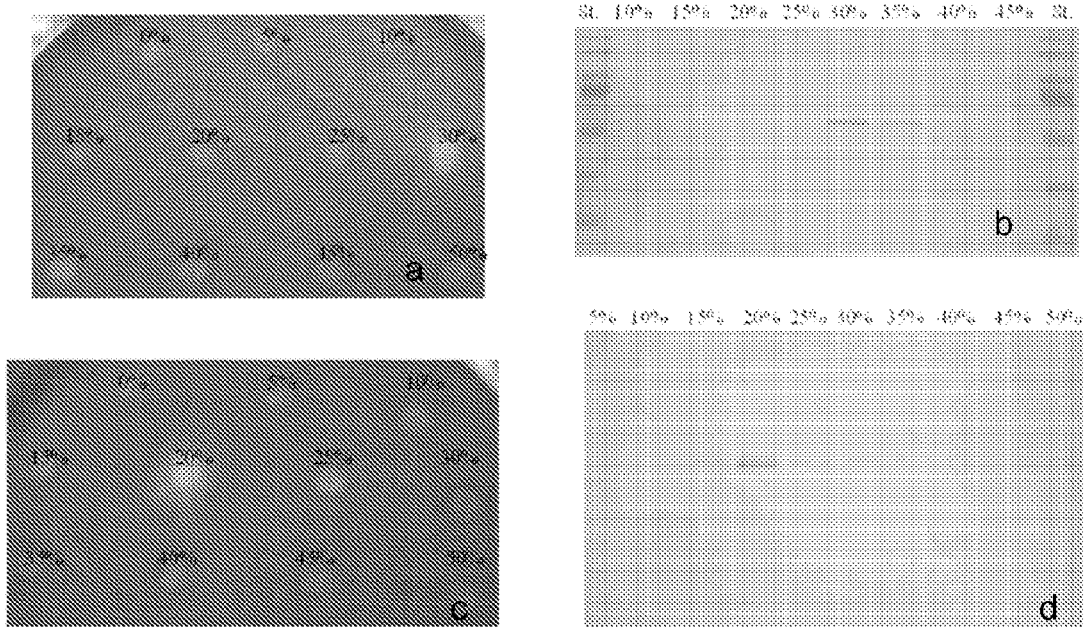
FIG. 5:
a, b: γPLE wild-type
c, d: γPLE-V263D
a, c: PH-shift assays
b, d: Western Blotting
Figure 6:
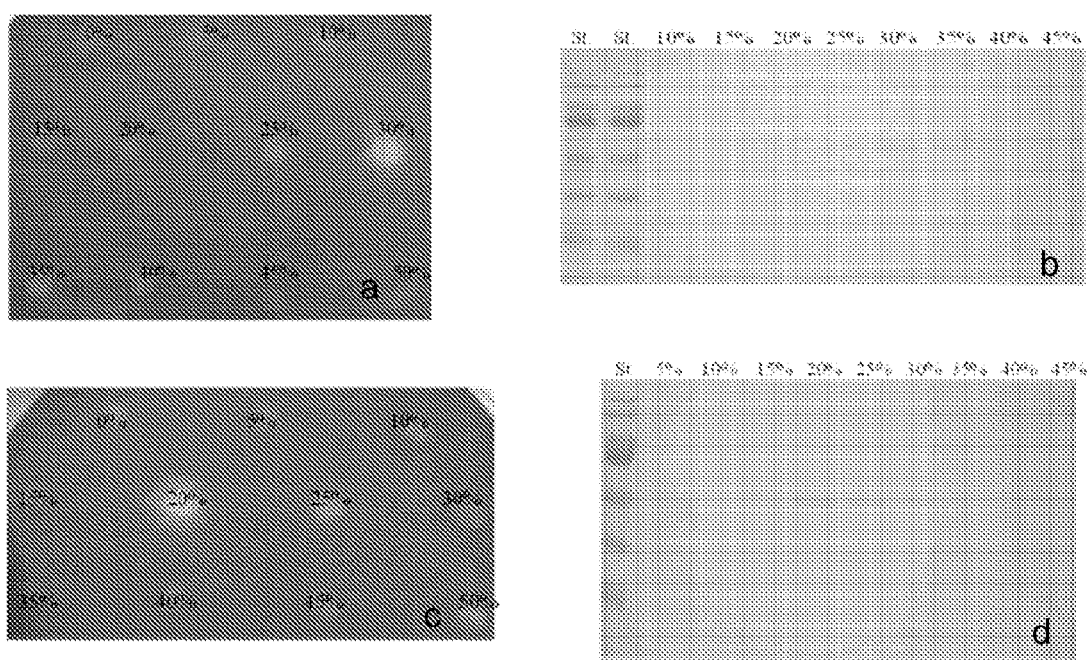
FIG. 6:
a, b: PICE wild-type
c, d: PICE-V263D
a, c: PH-shift assays
b, d: Western Blotting
Figure 7:
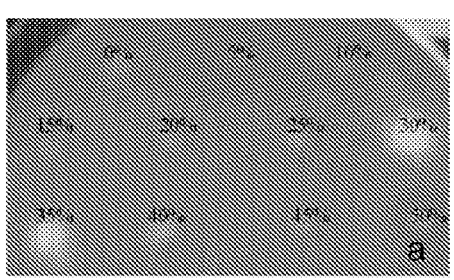
FIG. 7:
a, b: PLE2 wild-type
c, d: PLE2-V263D
a, c: PH-shift assays
b, d: Western Blotting
Figure 7:
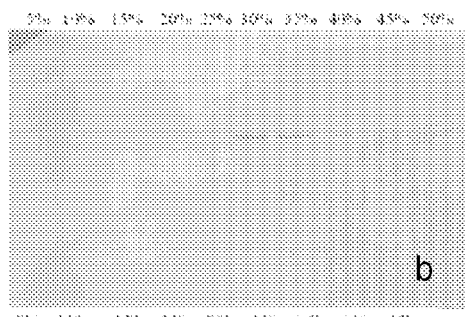
Figure 7:
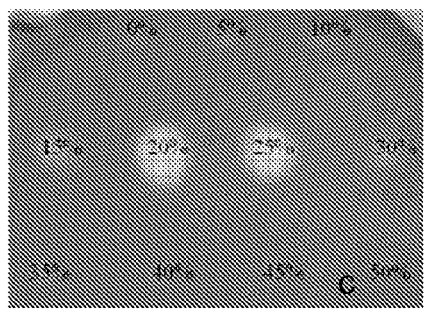
Figure 7:
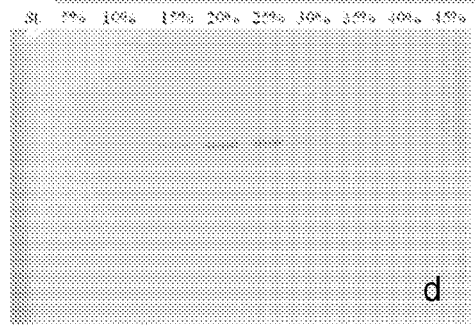
Figure 8:
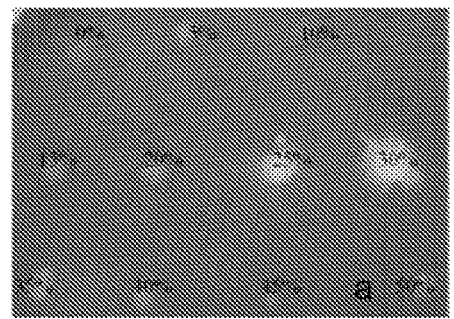
FIG. 8:
a, b: PLE3 wild-type
c, d: PLE3-V263D
a, c: PH-shift assays
b, d: Western Blotting
Figure 8:
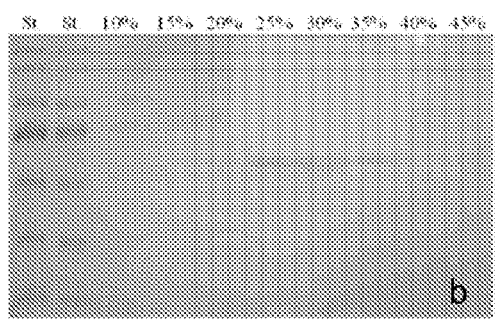
Figure 8:
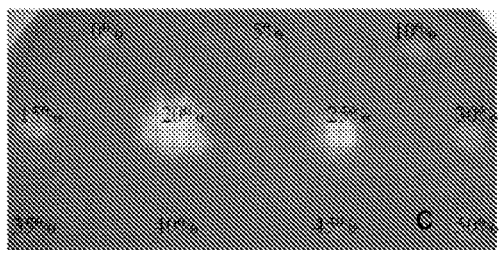
Figure 8:
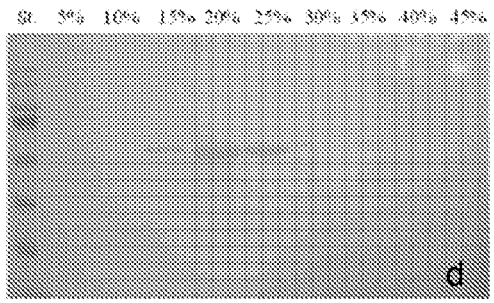
Figure 9:
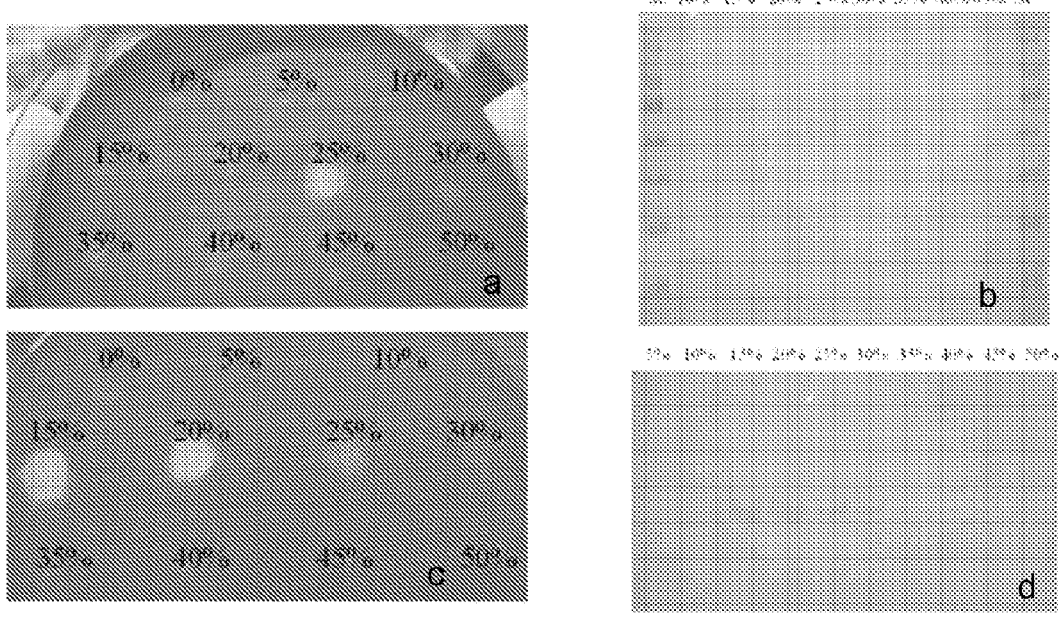
FIG. 9:
a, b PLE4 wild-type
c, d PLE4-V263D
a, c PH-shift assays
b, d Western Blotting
Figure 10:
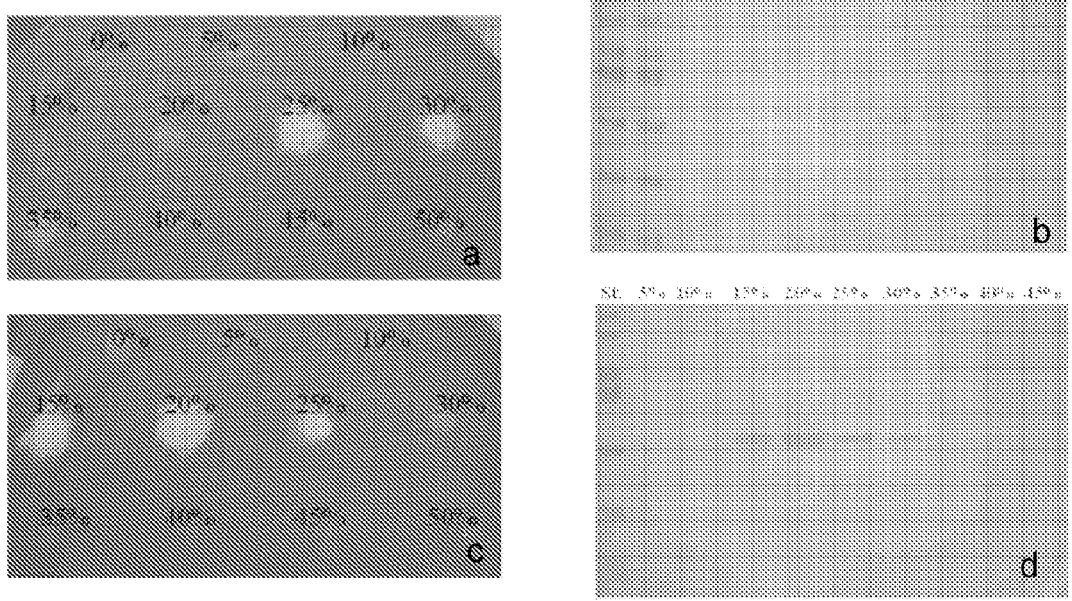
FIG. 10:
a, b PLE5 wild-type
c, d PLE5-V263D
a, c PH-shift assays
b, d Western Blotting
Figure 11A:
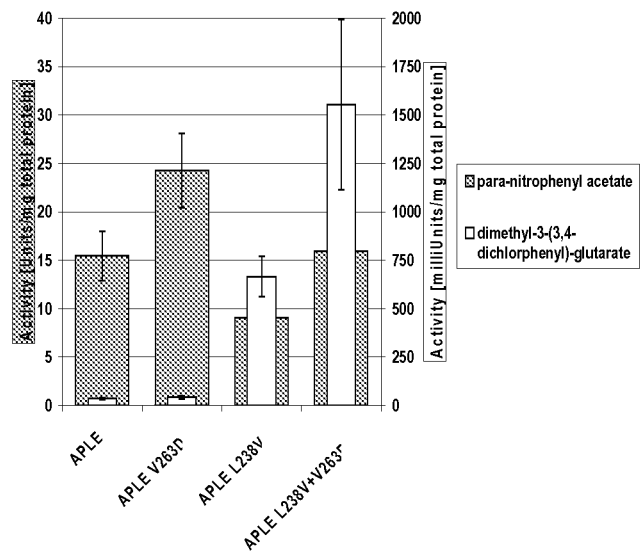
FIG. 11a: Results of measurement of the activity towards para-nitrophenyl acetate (light grey) and dimethyl-3-(3,4-dichlorphenyl)-glutarate (grey).
Figure 11B:
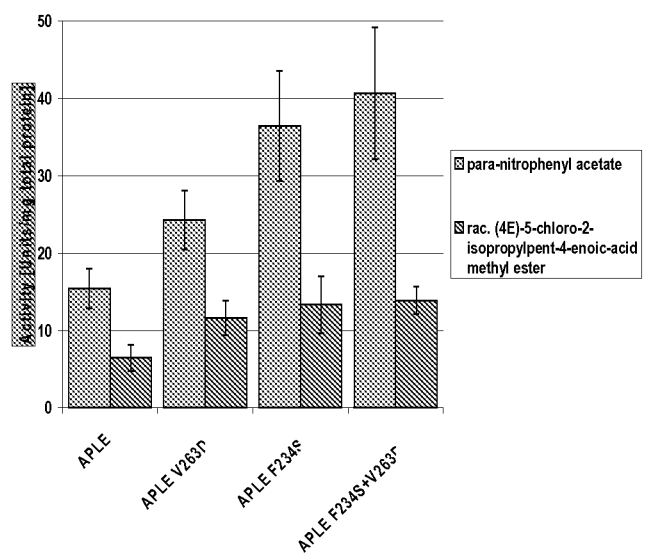
FIG. 11b: Results of measurement of the activity towards para-nitrophenyl acetate (light grey) and rac. (4E)-5-chloro-2-isopropylpent-4-enoic-acid methyl ester (dark grey).

<210> SEQ ID NO 1
<211> LENGTH: 6407
<212> TYPE: DNA
<213> ORGANISM: Unknown
<220> FEATURE:
<223> OTHER INFORMATION: Plasmid
<220> FEATURE:
<221> NAME/KEY: exon
<222> LOCATION: (4754)..(6397)
<223> OTHER INFORMATION: APLE (alternative Pig Liver Esterase]
<220> FEATURE:
<221> NAME/KEY: CDS
<222> LOCATION: (4754)..(6397)

<400> SEQUENCE: 1

```
ggctgttttg gcggatgaga gaagattttc agcctgatac agattaaatc agaacgcaga      60
agcggtctga taaaacagaa tttgcctggc ggcagtagcg cggtggtccc acctgacccc     120
atgccgaact cagaagtgaa acgccgtagc gccgatggta gtgtggggtc tccccatgcg     180
agagtaggga actgccaggc atcaaataaa acgaaaggct cagtcgaaag actgggcctt     240
tcgttttatc tgttgtttgt cggtgaacgc tctcctgagt aggacaaatc cgccgggagc     300
ggatttgaac gttgcgaagc aacggcccgg agggtggcgg gcaggacgcc cgccataaac     360
tgccaggcat caaattaagc agaaggccat cctgacggat ggcctttttg cgtttctaca     420
aactcttttt gtttatttt ctaaatacat tcaaatatgt atccgctcat gacgaataaa     480
tacctgtgac ggaagatcac ttcgcagaat aaataaatcc tggtgtccct gttgatacccg     540
ggaagccctg gccaacttt tggcgaaaat gagacgttga tcggcacgta agaggttcca     600
actttcacca taatgaaata agatcactac cgggcgtatt ttttgagtta tcgagatttt     660
caggagctaa ggaagctaaa atggagaaaa aaatcactgg atataccacc gttgatatat     720
cccaatggca tcgtaaagaa cattttgagg catttcagtc agttgctcaa tgtacctata     780
accagaccgt tcagctggat attacggcct ttttaaagac cgtaaagaaa ataagcaca     840
agttttatcc ggcctttatt cacattcttg cccgcctgat gaatgctcat ccggaattcc     900
gtatggcaat gaaagacggt gagctggtga tatgggatag tgttcacccct tgttacaccg     960
ttttccatga gcaaactgaa acgttttcat cgctctggag tgaataccac gacgatttcc    1020
ggcagtttct acacatatat tcgcaagatg tggcgtgtta cggtgaaaac ctggcctatt    1080
tccctaaagg gtttattgag aatatgtttt tcgtctcagc caatccctgg gtgagtttca    1140
ccagttttga tttaaacgtg gccaatatgg acaacttctt cgcccccgtt ttcaccatgg    1200
gcaaatatta tacgcaaggc gacaaggtgc tgatgccgct ggcgattcag gttcatcatg    1260
ccgtttgtga tggcttccat gtcggcagaa tgcttaatga attacaacag tactgcgatg    1320
agtggcaggc ggggcgtaa ttttttaag gcagttattg gtgcccttaa acgcctggtg    1380
ctacgcctga ataagtgata ataagcggat gaatggcaga aattcgaaag caaattcgac    1440
ccggtcgtcg gttcagggca gggtcgttaa atagccgctt atgtctattg ctggtttacc    1500
ggtttattga ctaccggaag cagtgtgacc gtgtgcttct caaatgcctg aggccagtta    1560
```

-continued

```
gatctcatga ccaaaatccc ttaacgtgag ttttcgttcc actgagcgtc agaccccgta       1620
gaaaagatca aaggatcttc ttgagatcct ttttttctgc gcgtaatctg ctgcttgcaa      1680
acaaaaaaac caccgctacc agcggtggtt tgtttgccgg atcaagagct accaactctt      1740
tttccgaagg taactggctt cagcagagcg cagataccaa atactgtcct tctagtgtag      1800
ccgtagttag gccaccactt caagaactct gtagcaccgc ctacatacct cgctctgcta      1860
atcctgttac cagtggctgc tgccagtggc gataagtcgt gtcttaccgg gttggactca      1920
agacgatagt taccggataa ggcgcagcgg tcgggctgaa cggggggttc gtgcacacag      1980
cccagcttgg agcgaacgac ctacaccgaa ctgagatacc tacagcgtga gcattgagaa      2040
agcgccacgc ttcccgaagg gagaaaggcg gacaggtatc cggtaagcgg cagggtcgga      2100
acaggagagc gcacgaggga gcttccaggg ggaaacgcct ggtatcttta tagtcctgtc      2160
gggtttcgcc acctctgact tgagcgtcga ttttttgtgat gctcgtcagg ggggcggagc      2220
ctatggaaaa acgccagcaa cgcggccttt ttacggttcc tggccttttg ctggccttt       2280 gctcacatgt tctttcctgc gttatcccct gattctgtgg ataaccgtat taccgccttt      2340
gagtgagctg ataccgctcg ccgcagccga cgaccgagc gcagcgagtc agtgagcgag       2400
gaagcggaag agcgcctgat gcggtatttt ctccttacgc atctgtgcgg tatttcacac      2460
cgcacgaacg ccagcaagac gtagcccagc gcgtcggcca gcttgcaatt cgcgctaact      2520
tacattaatt gcgttgcgct cactgcccgc tttccagtcg ggaaacctgt cgtgccagct      2580
gcattaatga atcggccaac gcgcgggag aggcggtttg cgtattgggc gccagggtgg       2640 ttttctttt caccagtgag acgggcaaca gctgattgcc cttcaccgcc tggccctgag       2700
agagttgcag caagcggtcc acgctggttt gccccagcag gcgaaaatcc tgtttgctgg      2760
tggttaacgg cggatataa catgagctgt cttcggtatc gtcgtatccc actaccgaga      2820
tatccgcacc aacgcgcagc ccggactcgg taatggcgcg cattgcgccc agcgccatct      2880
gatcgttggc aaccagcatc gcagtgggaa cgatgccctc attcagcatt tgcatggttt      2940
gttgaaaacc ggacatggca ctccagtcgc cttcccgttc cgctatcggc tgaatttgat      3000
tgcgagtgag atatttatgc cagccagcca gacgcagacg cgccgagaca gaacttaatg      3060
ggcccgctaa cagcgcgatt tgctggtgac ccaatgcgac cagatgctcc acgcccagtc      3120
gcgtaccgtc ttcatgggag aaaataatac tgttgatggg tgtctggtca gagacatcaa      3180
gaaataacgc cggaacatta gtgcaggcag cttccacagc aatggcatcc tggtcatcca      3240
gcggatagtt aatgatcagc ccactgacgc gttgcgcgag aagattgtgc accgccgctt      3300
tacaggcttc gacgccgctt cgttctacca tcgacaccac cacgctggca cccagttgat      3360
cggcgcgaga tttaatcgcc gcgacaattt gcgacggcgc gtgcagggcc agactggagg      3420
tggcaacgcc aatcagcaac gactgtttgc ccgccagttg ttgtgccacg cggttgggaa      3480
tgtaattcag ctccgccatc gccgcttcca cttttcccg cgttttcgca gaaacgtggc       3540
tggcctggtt caccacgcgg gaaacggtct gataagagac accggcatac tctgcgacat      3600
cgtataacgt tactggtttc acattcacca ccctgaattg actctcttcc gggcgctatc      3660
atgccatacc gcgaaaggtt ttgcaccatt cgatggtgtc aacgtaaatg ccgcttcgcc      3720
ttcgcgcgcg aattgcaagc tgatccgggc ttatcgactg cacggtgcac caatgcttct      3780
ggcgtcaggc agccatcgga agctgtggta tggctgtgca ggtcgtaaat cactgcataa      3840
ttcgtgtcgc tcaaggcgca ctcccgttct ggataatgtt ttttgcgccg acatcataac      3900
ggttctggca aatattctga aatgagctgt tgacaattaa tcatcggctc gtataatgtg      3960
```

```
tggaattgtg agcggataac aatttcacac aggaaacaga attcgagctc ggtacccggg    4020
gatcctttaa ctttaagaag gagatataat ggatgacgcg gcaattcaac aaacgttagc    4080
caaaatgggc atcaaaagca gcgatattca gcccgcgcct gtagctggca tgaagacagt    4140
tctgactaac agcggcgtgt tgtacatcac cgatgatggt aaacatatca ttcaggggcc    4200
aatgtatgac gttagtggca cggctccggt caatgtcacc aataagatgc tgttaaagca    4260
gttgaatgcg cttgaaaaag agatgatcgt ttataaagcg ccgcaggaaa acacgtcat    4320 caccgtgttt actgatatta cctgtggtta ctgccacaaa ctgcatgagc aaatggcaga    4380
ctacaacgcg ctggggatca ccgtgcgtta tcttgctttc ccgcgccagg ggctggacag    4440
cgatgcagag aaagaaatga agctatctg gtgtgcgaaa gataaaaaca aagcgtttga    4500
tgatgtgatg gcaggtaaaa gcgtcgcacc agccagttgc gacgtggata ttgccgacca    4560
ttacgcactt ggcgtccagc ttggcgttag cggtactccg gcagttgtgc tgagcaatgg    4620
cacacttgtt ccgggttacc agccgccgaa agagatgaaa gaattcctcg acgaacacca    4680
aaaaatgacc agcggtaaat aaggatcctc tagaaataat tttgtttaac tttaagaagg    4740
agatatacat atg gga caa cca gct tcg ccg cct gtc gtt gat acc gct         4789
            Gly Gln Pro Ala Ser Pro Pro Val Val Asp Thr Ala
              1               5                  10 caa gga cga gtc ttg ggt aag tac gtc tct tta gag gga ttg gca caa        4837
Gln Gly Arg Val Leu Gly Lys Tyr Val Ser Leu Glu Gly Leu Ala Gln
         15                  20                  25 ccg gtt gct gtc ttc ttg gga gtc cct ttt gct aag cca cct ctt gga        4885
Pro Val Ala Val Phe Leu Gly Val Pro Phe Ala Lys Pro Pro Leu Gly
     30                  35                  40 tct ttg agg ttt gcc ccg ccg caa cca gca gag cca tgg tct ttc gtt        4933
Ser Leu Arg Phe Ala Pro Pro Gln Pro Ala Glu Pro Trp Ser Phe Val
45                  50                  55                  60 aag aac act act tcc tac cct cca atg tgt tgt caa gaa cca atc gga        4981
Lys Asn Thr Thr Ser Tyr Pro Pro Met Cys Cys Gln Glu Pro Ile Gly
                 65                  70                  75 gga caa atg ctt tca gac cta ttc act aac aga aag gaa agg ctt atc        5029
Gly Gln Met Leu Ser Asp Leu Phe Thr Asn Arg Lys Glu Arg Leu Ile
             80                  85                  90 ccg gag ttc tct gag gat tgc ctt tac cta aat att tac act cct gcc        5077
Pro Glu Phe Ser Glu Asp Cys Leu Tyr Leu Asn Ile Tyr Thr Pro Ala
         95                  100                 105 gat ttg aca aag agg ggt agg ttg ccg gtt atg gtt tgg att cat gga        5125
Asp Leu Thr Lys Arg Gly Arg Leu Pro Val Met Val Trp Ile His Gly
    110                 115                 120 gga ggt ttg gtt gtt ggc gga gca tcc act tat gac gga ttg gct ctt        5173
Gly Gly Leu Val Val Gly Gly Ala Ser Thr Tyr Asp Gly Leu Ala Leu
125                 130                 135                 140 gcc gcg cac gag aac gtt gtt gtt gct att caa tac cgt ttg ggt            5221
Ala Ala His Glu Asn Val Val Val Ala Ile Gln Tyr Arg Leu Gly
                145                 150                 155 att tgg gga ttt ttc tcc aca gga gat gag cat tcc cgt gga aac tgg        5269
Ile Trp Gly Phe Phe Ser Thr Gly Asp Glu His Ser Arg Gly Asn Trp
         160                 165                 170 ggc cat tta gat caa gtt gct gca ttg cat tgg gtc caa gaa aac att        5317
Gly His Leu Asp Gln Val Ala Ala Leu His Trp Val Gln Glu Asn Ile
    175                 180                 185 gct aac ttc gga ggt gat cca ggt tct gtt act att ttc gga gaa tca        5365
Ala Asn Phe Gly Gly Asp Pro Gly Ser Val Thr Ile Phe Gly Glu Ser
190                 195                 200
```

```
-continued gca ggc gga gag agt gtc tct gta ttg gtt tta tca cca tta gct aag      5413
Ala Gly Gly Glu Ser Val Ser Val Leu Val Leu Ser Pro Leu Ala Lys
205             210                 215                 220 aac ctt ttt cat cgt gct att tcc gaa agt ggt gtt gct ttt acc gcc      5461
Asn Leu Phe His Arg Ala Ile Ser Glu Ser Gly Val Ala Phe Thr Ala
                225                 230                 235 ggt ttg gtc agg aag gat atg aag gcc gca gcc aag cag atc gct gtc      5509
Gly Leu Val Arg Lys Asp Met Lys Ala Ala Ala Lys Gln Ile Ala Val
            240                 245                 250 ctt gca gga tgc aaa act act act tcg gca gtc ttc gtg cat tgt ttg      5557
Leu Ala Gly Cys Lys Thr Thr Thr Ser Ala Val Phe Val His Cys Leu
        255                 260                 265 cgt caa aag tcg gaa gat gaa ctt tta gac ctc acg ttg aag atg aaa      5605
Arg Gln Lys Ser Glu Asp Glu Leu Leu Asp Leu Thr Leu Lys Met Lys
    270                 275                 280 ttc ttt gcc ctt gac tta cac gga gat cca agg gaa tct cac cct ttt      5653
Phe Phe Ala Leu Asp Leu His Gly Asp Pro Arg Glu Ser His Pro Phe
285                 290                 295                 300 ttg acc act gtt gtt gac gga gtt ttg ttg cct aag atg cct gag gaa      5701
Leu Thr Thr Val Val Asp Gly Val Leu Leu Pro Lys Met Pro Glu Glu
                305                 310                 315 atc ttg gcc gag aag gac ttt aac acc gtc cca tac att gtt gga att      5749
Ile Leu Ala Glu Lys Asp Phe Asn Thr Val Pro Tyr Ile Val Gly Ile
                320                 325                 330 aac aag cag gag ttc gga tgg ctt ttg cca acg atg atg gga ttt cct      5797
Asn Lys Gln Glu Phe Gly Trp Leu Leu Pro Thr Met Met Gly Phe Pro
            335                 340                 345 ctt tcc gag gga aag ttg gat caa aag acg gct acg tca ctt ttg tgg      5845
Leu Ser Glu Gly Lys Leu Asp Gln Lys Thr Ala Thr Ser Leu Leu Trp
        350                 355                 360 aag tcc tac cca att gcc aac att cct gaa gag ttg acc cca gtt gct      5893
Lys Ser Tyr Pro Ile Ala Asn Ile Pro Glu Glu Leu Thr Pro Val Ala
365                 370                 375                 380 acc gat aag tat tta gga gga aca gat gat cct gtc aaa aag aaa gat      5941
Thr Asp Lys Tyr Leu Gly Gly Thr Asp Asp Pro Val Lys Lys Lys Asp
                385                 390                 395 ttg ttt ttg gat ctg atg gga gac gtt gtt ttc ggc gtc cca tca gtt      5989
Leu Phe Leu Asp Leu Met Gly Asp Val Val Phe Gly Val Pro Ser Val
            400                 405                 410 acg gtt gct cgt cag cat agg gac gca gga gct cca act tac atg tat      6037
Thr Val Ala Arg Gln His Arg Asp Ala Gly Ala Pro Thr Tyr Met Tyr
        415                 420                 425 gag ttc caa tat cgt cca tct ttt tca tcg gat aag aaa cct aag acg      6085
Glu Phe Gln Tyr Arg Pro Ser Phe Ser Ser Asp Lys Lys Pro Lys Thr
    430                 435                 440 gtt att gga gat cat gga gac gaa att ttt tcc gtc ttc ggc ttc cca      6133
Val Ile Gly Asp His Gly Asp Glu Ile Phe Ser Val Phe Gly Phe Pro
445                 450                 455                 460 ttg ctc aaa ggt gac gct cca gag gaa gaa gtc agt ctt tct aag acg      6181
Leu Leu Lys Gly Asp Ala Pro Glu Glu Glu Val Ser Leu Ser Lys Thr
                465                 470                 475 gtt atg aaa ttt tgg gct aac ttc gcc cgt agt gga aac cct aat gga      6229
Val Met Lys Phe Trp Ala Asn Phe Ala Arg Ser Gly Asn Pro Asn Gly
            480                 485                 490 gaa gga ttg cct cac tgg ccg atg tac gat caa gag gag gga tac ctt      6277
Glu Gly Leu Pro His Trp Pro Met Tyr Asp Gln Glu Glu Gly Tyr Leu
        495                 500                 505 caa att ggt gtc aac act caa gca gct aag agg ttg aaa ggc gag gag      6325
Gln Ile Gly Val Asn Thr Gln Ala Ala Lys Arg Leu Lys Gly Glu Glu
    510                 515                 520
```

```
gtt gct ttt tgg aac gac ctg ttg tcc aag gaa gca gca aag aag cca    6373
Val Ala Phe Trp Asn Asp Leu Leu Ser Lys Glu Ala Ala Lys Lys Pro
525                 530                 535                 540 cct aag ata aag cac gcc gaa ttg taataagctt                         6407
Pro Lys Ile Lys His Ala Glu Leu
                545

<210> SEQ ID NO 2
<211> LENGTH: 548
<212> TYPE: PRT
<213> ORGANISM: Unknown
<220> FEATURE:
<223> OTHER INFORMATION: Synthetic Construct

<400> SEQUENCE: 2

Gly Gln Pro Ala Ser Pro Pro Val Val Asp Thr Ala Gln Gly Arg Val
1               5                   10                  15

Leu Gly Lys Tyr Val Ser Leu Glu Gly Leu Ala Gln Pro Val Ala Val
                20                  25                  30

Phe Leu Gly Val Pro Phe Ala Lys Pro Pro Leu Gly Ser Leu Arg Phe
            35                  40                  45

Ala Pro Pro Gln Pro Ala Glu Pro Trp Ser Phe Val Lys Asn Thr Thr
50                  55                  60

Ser Tyr Pro Pro Met Cys Cys Gln Glu Pro Ile Gly Gly Gln Met Leu
65                  70                  75                  80

Ser Asp Leu Phe Thr Asn Arg Lys Glu Arg Leu Ile Pro Glu Phe Ser
                85                  90                  95

Glu Asp Cys Leu Tyr Leu Asn Ile Tyr Thr Pro Ala Asp Leu Thr Lys
            100                 105                 110

Arg Gly Arg Leu Pro Val Met Val Trp Ile His Gly Gly Gly Leu Val
        115                 120                 125

Val Gly Gly Ala Ser Thr Tyr Asp Gly Leu Ala Leu Ala Ala His Glu
130                 135                 140

Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp
                165                 170                 175

Gln Val Ala Ala Leu His Trp Val Gln Glu Asn Ile Ala Asn Phe Gly
            180                 185                 190

Gly Asp Pro Gly Ser Val Thr Ile Phe Gly Glu Ser Ala Gly Gly Glu
        195                 200                 205

Ser Val Ser Val Leu Val Leu Ser Pro Leu Ala Lys Asn Leu Phe His
210                 215                 220

Arg Ala Ile Ser Glu Ser Gly Val Ala Phe Thr Ala Gly Leu Val Arg
225                 230                 235                 240

Lys Asp Met Lys Ala Ala Ala Lys Gln Ile Ala Val Leu Ala Gly Cys
                245                 250                 255

Lys Thr Thr Thr Ser Ala Val Phe Val His Cys Leu Arg Gln Lys Ser
            260                 265                 270

Glu Asp Glu Leu Leu Asp Leu Thr Leu Lys Met Lys Phe Phe Ala Leu
        275                 280                 285

Asp Leu His Gly Asp Pro Arg Glu Ser His Pro Phe Leu Thr Thr Val
290                 295                 300

Val Asp Gly Val Leu Leu Pro Lys Met Pro Glu Glu Ile Leu Ala Glu
305                 310                 315                 320
```

```
Lys Asp Phe Asn Thr Val Pro Tyr Ile Val Gly Ile Asn Lys Gln Glu
                325                 330                 335

Phe Gly Trp Leu Leu Pro Thr Met Met Gly Phe Pro Leu Ser Glu Gly
            340                 345                 350

Lys Leu Asp Gln Lys Thr Ala Thr Ser Leu Leu Trp Lys Ser Tyr Pro
                355                 360                 365

Ile Ala Asn Ile Pro Glu Glu Leu Thr Pro Val Ala Thr Asp Lys Tyr
370                 375                 380

Leu Gly Gly Thr Asp Asp Pro Val Lys Lys Asp Leu Phe Leu Asp
385                 390                 395                 400

Leu Met Gly Asp Val Val Phe Gly Val Pro Ser Val Thr Val Ala Arg
                405                 410                 415

Gln His Arg Asp Ala Gly Ala Pro Thr Tyr Met Tyr Glu Phe Gln Tyr
                420                 425                 430

Arg Pro Ser Phe Ser Ser Asp Lys Lys Pro Lys Thr Val Ile Gly Asp
                435                 440                 445

His Gly Asp Glu Ile Phe Ser Val Phe Gly Phe Pro Leu Leu Lys Gly
                450                 455                 460

Asp Ala Pro Glu Glu Glu Val Ser Leu Ser Lys Thr Val Met Lys Phe
465                 470                 475                 480

Trp Ala Asn Phe Ala Arg Ser Gly Asn Pro Asn Gly Glu Gly Leu Pro
                485                 490                 495

His Trp Pro Met Tyr Asp Gln Glu Glu Gly Tyr Leu Gln Ile Gly Val
                500                 505                 510

Asn Thr Gln Ala Ala Lys Arg Leu Lys Gly Glu Glu Val Ala Phe Trp
                515                 520                 525

Asn Asp Leu Leu Ser Lys Glu Ala Ala Lys Lys Pro Pro Lys Ile Lys
530                 535                 540

His Ala Glu Leu
545

<210> SEQ ID NO 3
<211> LENGTH: 1660
<212> TYPE: DNA
<213> ORGANISM: Unknown
<220> FEATURE:
<223> OTHER INFORMATION: Synthetic gene
<220> FEATURE:
<221> NAME/KEY: exon
<222> LOCATION: (7)..(1650)
<223> OTHER INFORMATION: gamma PLE
<220> FEATURE:
<221> NAME/KEY: CDS
<222> LOCATION: (7)..(1650)
<223> OTHER INFORMATION: gamma PLE

<400> SEQUENCE: 3 catatg gga caa cca gct tcg ccg cct gtc gtt gat acc gct caa gga         48
       Gly Gln Pro Ala Ser Pro Pro Val Val Asp Thr Ala Gln Gly
       1               5                   10 cga gtc ttg ggt aag tac gtc tct tta gag gga ttg gca caa ccg gtt        96
Arg Val Leu Gly Lys Tyr Val Ser Leu Glu Gly Leu Ala Gln Pro Val
15                  20                  25                  30 gct gtc ttc ttg gga gtc cct ttt gct aag cca cct ctt gga tct ttg       144
Ala Val Phe Leu Gly Val Pro Phe Ala Lys Pro Pro Leu Gly Ser Leu
                35                  40                  45 agg ttt gcc ccg ccg caa cca gca gag cca tgg tct ttc gtt aag aac       192
Arg Phe Ala Pro Pro Gln Pro Ala Glu Pro Trp Ser Phe Val Lys Asn
            50                  55                  60
```

| | |
|---|---|
| act act tcc tac cct cca atg tgt tgt caa gat cca gtc gta gaa caa<br>Thr Thr Ser Tyr Pro Pro Met Cys Cys Gln Asp Pro Val Val Glu Gln<br>             65                     70                 75 | 240 |
| atg acg tca gac cta ttc act aac gga aag gaa agg ctt acc ctg gag<br>Met Thr Ser Asp Leu Phe Thr Asn Gly Lys Glu Arg Leu Thr Leu Glu<br> 80                     85                     90 | 288 |
| ttc tct gag gat tgc ctt tac cta aat att tac act cct gcc gat ttg<br>Phe Ser Glu Asp Cys Leu Tyr Leu Asn Ile Tyr Thr Pro Ala Asp Leu<br>95                   100                 105               110 | 336 |
| aca aag agg ggt agg ttg ccg gtt atg gtt tgg att cat gga gga ggt<br>Thr Lys Arg Gly Arg Leu Pro Val Met Val Trp Ile His Gly Gly Gly<br>             115                     120               125 | 384 |
| ttg gtt ctg ggc gga gca ccg atg tat gac gga gtg gtt ctt gcc gcg<br>Leu Val Leu Gly Gly Ala Pro Met Tyr Asp Gly Val Val Leu Ala Ala<br>                 130                     135               140 | 432 |
| cac gag aac gtt gtt gtt gtt gct att caa tac cgt ttg ggt att tgg<br>His Glu Asn Val Val Val Val Ala Ile Gln Tyr Arg Leu Gly Ile Trp<br>         145                     150               155 | 480 |
| gga ttt ttc tcc aca gga gat gag cat tcc cgt gga aac tgg ggc cat<br>Gly Phe Phe Ser Thr Gly Asp Glu His Ser Arg Gly Asn Trp Gly His<br>160                     165                 170 | 528 |
| tta gat caa gtt gct gca ttg cat tgg gtc caa gaa aac att gct aac<br>Leu Asp Gln Val Ala Ala Leu His Trp Val Gln Glu Asn Ile Ala Asn<br>175                     180                 185               190 | 576 |
| ttc gga ggt gat cca ggt tct gtt act att ttc gga gaa tca gca ggc<br>Phe Gly Gly Asp Pro Gly Ser Val Thr Ile Phe Gly Glu Ser Ala Gly<br>                      195                 200               205 | 624 |
| gga gag agt gtc tct gta ttg gtt tta tca cca tta gct aag aac ctt<br>Gly Glu Ser Val Ser Val Leu Val Leu Ser Pro Leu Ala Lys Asn Leu<br>             210                     215               220 | 672 |
| ttt cat cgt gct att tcc gaa agt ggt gtt gct tta acc gtc gct ttg<br>Phe His Arg Ala Ile Ser Glu Ser Gly Val Ala Leu Thr Val Ala Leu<br>                 225                     230               235 | 720 |
| gtc agg aag gat atg aag gcc gca gcc aag cag atc gct gtc ctt gca<br>Val Arg Lys Asp Met Lys Ala Ala Ala Lys Gln Ile Ala Val Leu Ala<br>240                     245                 250 | 768 |
| gga tgc aaa act act act tcg gca gtc ttc gtg cat tgt ttg cgt caa<br>Gly Cys Lys Thr Thr Thr Ser Ala Val Phe Val His Cys Leu Arg Gln<br>255                     260                 265               270 | 816 |
| aag tcg gaa gat gaa ctt tta gac ctc acg ttg aag atg aaa ttc ctg<br>Lys Ser Glu Asp Glu Leu Leu Asp Leu Thr Leu Lys Met Lys Phe Leu<br>                 275                     280               285 | 864 |
| acc ctt gac ttt cac gga gat caa agg gaa tct cac cct ttt ttg ccg<br>Thr Leu Asp Phe His Gly Asp Gln Arg Glu Ser His Pro Phe Leu Pro<br>             290                     295               300 | 912 |
| act gtt gtt gac gga gtt ttg ttg cct aag atg cct gag gaa atc ttg<br>Thr Val Val Asp Gly Val Leu Leu Pro Lys Met Pro Glu Glu Ile Leu<br>         305                     310               315 | 960 |
| gcc gag aag gac ttt aac acc gtc cca tac att gtt gga att aac aag<br>Ala Glu Lys Asp Phe Asn Thr Val Pro Tyr Ile Val Gly Ile Asn Lys<br>320                     325                 330 | 1008 |
| cag gag ttc gga tgg ctt ttg cca acg atg atg gga ttt cct ctt tcc<br>Gln Glu Phe Gly Trp Leu Leu Pro Thr Met Met Gly Phe Pro Leu Ser<br>335                     340                 345               350 | 1056 |
| gag gga aag ttg gat caa aag acg gct acg tca ctt tgg aag tcc<br>Glu Gly Lys Leu Asp Gln Lys Thr Ala Thr Ser Leu Leu Trp Lys Ser<br>                 355                     360               365 | 1104 |
| tac cca att gcc aac att cct gaa gag ttg acc cca gtt gct acc gat<br>Tyr Pro Ile Ala Asn Ile Pro Glu Glu Leu Thr Pro Val Ala Thr Asp<br>             370                     375               380 | 1152 |

```
aag tat tta gga gga aca gat gat cct gtc aaa aag aaa gat ttg ttt    1200
Lys Tyr Leu Gly Gly Thr Asp Asp Pro Val Lys Lys Lys Asp Leu Phe
        385                 390                 395 ttg gat ctg atg gga gac gtt gtt ttc ggc gtc cca tca gtt acg gtt    1248
Leu Asp Leu Met Gly Asp Val Val Phe Gly Val Pro Ser Val Thr Val
400                 405                 410 gct cgt cag cat agg gac gca gga gct cca act tac atg tat gag ttc    1296
Ala Arg Gln His Arg Asp Ala Gly Ala Pro Thr Tyr Met Tyr Glu Phe
415                 420                 425                 430 caa tat cgt cca tct ttt tca tcg gat aag aaa cct aag acg gtt att    1344
Gln Tyr Arg Pro Ser Phe Ser Ser Asp Lys Lys Pro Lys Thr Val Ile
                435                 440                 445 gga gat cat gga gac gaa att ttt tcc gtc ttc ggc ttc cca ttg ctc    1392
Gly Asp His Gly Asp Glu Ile Phe Ser Val Phe Gly Phe Pro Leu Leu
            450                 455                 460 aaa ggt gac gct cca gag gaa gaa gtc agt ctt tct aag acg gtt atg    1440
Lys Gly Asp Ala Pro Glu Glu Glu Val Ser Leu Ser Lys Thr Val Met
        465                 470                 475 aaa ttt tgg gct aac ttc gcc cgt agt gga aac cct aat gga gaa gga    1488
Lys Phe Trp Ala Asn Phe Ala Arg Ser Gly Asn Pro Asn Gly Glu Gly
    480                 485                 490 ttg cct cac tgg ccg atg tac gat caa gag gag gga tac ctt caa att    1536
Leu Pro His Trp Pro Met Tyr Asp Gln Glu Glu Gly Tyr Leu Gln Ile
495                 500                 505                 510 ggt gtc aac act caa gca gct aag agg ttg aaa ggc gag gag gtt gct    1584
Gly Val Asn Thr Gln Ala Ala Lys Arg Leu Lys Gly Glu Glu Val Ala
                515                 520                 525 ttt tgg aac gac ctg ttg tcc aag gaa gca gca aag aag cca cct aag    1632
Phe Trp Asn Asp Leu Leu Ser Lys Glu Ala Ala Lys Lys Pro Pro Lys
            530                 535                 540 ata aag cac gcc gaa ttg taataagctt                                 1660
Ile Lys His Ala Glu Leu
        545

<210> SEQ ID NO 4
<211> LENGTH: 548
<212> TYPE: PRT
<213> ORGANISM: Unknown
<220> FEATURE:
<223> OTHER INFORMATION: Synthetic Construct

<400> SEQUENCE: 4

Gly Gln Pro Ala Ser Pro Pro Val Val Asp Thr Ala Gln Gly Arg Val
1               5                   10                  15

Leu Gly Lys Tyr Val Ser Leu Glu Gly Leu Ala Gln Pro Val Ala Val
                20                  25                  30

Phe Leu Gly Val Pro Phe Ala Lys Pro Pro Leu Gly Ser Leu Arg Phe
            35                  40                  45

Ala Pro Pro Gln Pro Ala Glu Pro Trp Ser Phe Val Lys Asn Thr Thr
        50                  55                  60

Ser Tyr Pro Pro Met Cys Cys Gln Asp Pro Val Val Glu Gln Met Thr
65                  70                  75                  80

Ser Asp Leu Phe Thr Asn Gly Lys Glu Arg Leu Thr Leu Glu Phe Ser
                85                  90                  95

Glu Asp Cys Leu Tyr Leu Asn Ile Tyr Thr Pro Ala Asp Leu Thr Lys
            100                 105                 110

Arg Gly Arg Leu Pro Val Met Val Trp Ile His Gly Gly Gly Leu Val
        115                 120                 125
```

-continued

Leu Gly Gly Ala Pro Met Tyr Asp Gly Val Leu Ala Ala His Glu
130                 135                 140

Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp
                165                 170                 175

Gln Val Ala Ala Leu His Trp Val Gln Glu Asn Ile Ala Asn Phe Gly
                180                 185                 190

Gly Asp Pro Gly Ser Val Thr Ile Phe Gly Glu Ser Ala Gly Gly Glu
                195                 200                 205

Ser Val Ser Val Leu Val Leu Ser Pro Leu Ala Lys Asn Leu Phe His
210                 215                 220

Arg Ala Ile Ser Glu Ser Gly Val Ala Leu Thr Val Ala Leu Val Arg
225                 230                 235                 240

Lys Asp Met Lys Ala Ala Lys Gln Ile Ala Val Leu Ala Gly Cys
                245                 250                 255

Lys Thr Thr Thr Ser Ala Val Phe Val His Cys Leu Arg Gln Lys Ser
                260                 265                 270

Glu Asp Glu Leu Leu Asp Leu Thr Leu Lys Met Lys Phe Leu Thr Leu
                275                 280                 285

Asp Phe His Gly Asp Gln Arg Glu Ser His Pro Phe Leu Pro Thr Val
290                 295                 300

Val Asp Gly Val Leu Leu Pro Lys Met Pro Glu Ile Leu Ala Glu
305                 310                 315                 320

Lys Asp Phe Asn Thr Val Pro Tyr Ile Val Gly Ile Asn Lys Gln Glu
                325                 330                 335

Phe Gly Trp Leu Leu Pro Thr Met Met Gly Phe Pro Leu Ser Glu Gly
                340                 345                 350

Lys Leu Asp Gln Lys Thr Ala Thr Ser Leu Leu Trp Lys Ser Tyr Pro
                355                 360                 365

Ile Ala Asn Ile Pro Glu Glu Leu Thr Pro Val Ala Thr Asp Lys Tyr
370                 375                 380

Leu Gly Gly Thr Asp Asp Pro Val Lys Lys Lys Asp Leu Phe Leu Asp
385                 390                 395                 400

Leu Met Gly Asp Val Val Phe Gly Val Pro Ser Val Thr Val Ala Arg
                405                 410                 415

Gln His Arg Asp Ala Gly Ala Pro Thr Tyr Met Tyr Glu Phe Gln Tyr
                420                 425                 430

Arg Pro Ser Phe Ser Ser Asp Lys Lys Pro Lys Thr Val Ile Gly Asp
                435                 440                 445

His Gly Asp Glu Ile Phe Ser Val Phe Gly Phe Pro Leu Leu Lys Gly
                450                 455                 460

Asp Ala Pro Glu Glu Glu Val Ser Leu Ser Lys Thr Val Met Lys Phe
465                 470                 475                 480

Trp Ala Asn Phe Ala Arg Ser Gly Asn Pro Asn Gly Glu Gly Leu Pro
                485                 490                 495

His Trp Pro Met Tyr Asp Gln Glu Glu Gly Tyr Leu Gln Ile Gly Val
                500                 505                 510

Asn Thr Gln Ala Ala Lys Arg Leu Lys Gly Glu Glu Val Ala Phe Trp
                515                 520                 525

Asn Asp Leu Leu Ser Lys Glu Ala Ala Lys Lys Pro Pro Lys Ile Lys
530                 535                 540

His Ala Glu Leu

```
545

<210> SEQ ID NO 5
<211> LENGTH: 1660
<212> TYPE: DNA
<213> ORGANISM: Unknown
<220> FEATURE:
<223> OTHER INFORMATION: Synthetic gene
<220> FEATURE:
<221> NAME/KEY: exon
<222> LOCATION: (7)..(1650)
<223> OTHER INFORMATION: Porcine Intestinal Colon Esterase
<220> FEATURE:
<221> NAME/KEY: CDS
<222> LOCATION: (7)..(1650)
<223> OTHER INFORMATION: Porcine Intestinal Colon Esterase

<400> SEQUENCE: 5 catatg gga caa cca gct tcg ccg cct gtc gtt gat acc gct caa gga        48
       Gly Gln Pro Ala Ser Pro Pro Val Val Asp Thr Ala Gln Gly
       1               5                   10 cga gtc ttg ggt aag tac gtc tct tta gag gga ttg gca caa ccg gtt      96
Arg Val Leu Gly Lys Tyr Val Ser Leu Glu Gly Leu Ala Gln Pro Val
15                  20                  25                  30 gct gtc ttc ttg gga gtc cct ttt gct aag cca cct ctt gga tct ttg      144
Ala Val Phe Leu Gly Val Pro Phe Ala Lys Pro Pro Leu Gly Ser Leu
                35                  40                  45 agg ttt gcc ccg ccg caa cca gca gag cca tgg tct ttc gtt aag aac      192
Arg Phe Ala Pro Pro Gln Pro Ala Glu Pro Trp Ser Phe Val Lys Asn
            50                  55                  60 act act tcc tac cct cca atg tgt tgt caa gat cca gtc gca gga caa      240
Thr Thr Ser Tyr Pro Pro Met Cys Cys Gln Asp Pro Val Ala Gly Gln
        65                  70                  75 atg acg tca gac cta ttc act aac gga aag gaa agg ctt atc ccg gag      288
Met Thr Ser Asp Leu Phe Thr Asn Gly Lys Glu Arg Leu Ile Pro Glu
    80                  85                  90 ttc tct gag gat tgc ctt tac cta aat att tac act cct gcc gat ttg      336
Phe Ser Glu Asp Cys Leu Tyr Leu Asn Ile Tyr Thr Pro Ala Asp Leu
95                  100                 105                 110 aca aag agg ggt agg ttg ccg gtt atg gtt tgg att cat gga gga ggt      384
Thr Lys Arg Gly Arg Leu Pro Val Met Val Trp Ile His Gly Gly Gly
                115                 120                 125 ttg gtt gtt ggc gga gca tcc act tat gac gga ttg gct ctt gcc gcg      432
Leu Val Val Gly Gly Ala Ser Thr Tyr Asp Gly Leu Ala Leu Ala Ala
            130                 135                 140 cac gag aac gtt gtt gtt gtt gct att caa tac cgt ttg ggt att tgg      480
His Glu Asn Val Val Val Val Ala Ile Gln Tyr Arg Leu Gly Ile Trp
        145                 150                 155 gga ttt ttc tcc aca gga gat gag cat tcc cgt gga aac tgg ggc cat      528
Gly Phe Phe Ser Thr Gly Asp Glu His Ser Arg Gly Asn Trp Gly His
    160                 165                 170 tta gat caa gtt gct gca ttg cat tgg gtc caa gaa aac att gct aac      576
Leu Asp Gln Val Ala Ala Leu His Trp Val Gln Glu Asn Ile Ala Asn
175                 180                 185                 190 ttc gga ggt gat aca ggt tct gtt act att ttc gga gaa tca gca ggc      624
Phe Gly Gly Asp Thr Gly Ser Val Thr Ile Phe Gly Glu Ser Ala Gly
                195                 200                 205 gga gag agt gtc tct gta ttg gtt tta tca cca tta gct aag aac ctt      672
Gly Glu Ser Val Ser Val Leu Val Leu Ser Pro Leu Ala Lys Asn Leu
            210                 215                 220 ttt cat cgt gct att tcc gaa agt ggt gtt gct tta acc gcc ggt ttg      720
Phe His Arg Ala Ile Ser Glu Ser Gly Val Ala Leu Thr Ala Gly Leu
        225                 230                 235
```

```
gtc agg aag gat atg aag gcc gca gcc aag cag atc gct gtc ctt gca      768
Val Arg Lys Asp Met Lys Ala Ala Ala Lys Gln Ile Ala Val Leu Ala
    240             245                 250 gga tgc aaa act act act tcg gca gtc ttc gtg cat tgt ttg cgt caa      816
Gly Cys Lys Thr Thr Thr Ser Ala Val Phe Val His Cys Leu Arg Gln
255             260                 265                 270 aag tcg gaa gat gaa ctt tta gac ctc acg ttg aag atg aaa ttc ctg      864
Lys Ser Glu Asp Glu Leu Leu Asp Leu Thr Leu Lys Met Lys Phe Leu
                275                 280                 285 acc ctt gac tta cac gga gat cca agg gaa tct cac cct ttt ttg ccg      912
Thr Leu Asp Leu His Gly Asp Pro Arg Glu Ser His Pro Phe Leu Pro
            290                 295                 300 act gtt gtt gac gga gtt ttg ttg cct aag atg cct gag gaa atc ttg      960
Thr Val Val Asp Gly Val Leu Leu Pro Lys Met Pro Glu Glu Ile Leu
        305                 310                 315 gcc gag aag gac ttt aac acc gtc cca tac att gtt gga att aac aag     1008
Ala Glu Lys Asp Phe Asn Thr Val Pro Tyr Ile Val Gly Ile Asn Lys
320                 325                 330 cag gag ttc gga tgg ctt ttg cca acg atg atg gga ttt cct ctt tcc     1056
Gln Glu Phe Gly Trp Leu Leu Pro Thr Met Met Gly Phe Pro Leu Ser
335                 340                 345                 350 gag gga aag ttg gat caa aag acg gct acg tca ctt ttg tgg aag tcc     1104
Glu Gly Lys Leu Asp Gln Lys Thr Ala Thr Ser Leu Leu Trp Lys Ser
                355                 360                 365 ttc cca att acc aac att cct gaa gag ttg acc cca gtt gct acc gat     1152
Phe Pro Ile Thr Asn Ile Pro Glu Glu Leu Thr Pro Val Ala Thr Asp
            370                 375                 380 aag tat tta gga gga aca gat gat cct gtc aaa aag aaa gat ttg ttt     1200
Lys Tyr Leu Gly Gly Thr Asp Asp Pro Val Lys Lys Lys Asp Leu Phe
        385                 390                 395 ttg gat ctg atg gga gac gtt gtt ttc ggc gtc cca tca gtt acg gtt     1248
Leu Asp Leu Met Gly Asp Val Val Phe Gly Val Pro Ser Val Thr Val
    400                 405                 410 gct cgt cag cat agg gac gca gga gct cca act tac atg tat gag ttc     1296
Ala Arg Gln His Arg Asp Ala Gly Ala Pro Thr Tyr Met Tyr Glu Phe
415                 420                 425                 430 caa tat cgt cca tct ttt tca tcg gat aag aaa cct aag acg gtt att     1344
Gln Tyr Arg Pro Ser Phe Ser Ser Asp Lys Lys Pro Lys Thr Val Ile
                435                 440                 445 gga gat cat gga gac gaa att ttt tcc gtc ttc ggc ttc cca ttg ctc     1392
Gly Asp His Gly Asp Glu Ile Phe Ser Val Phe Gly Phe Pro Leu Leu
            450                 455                 460 aaa ggt gac gct cca gag gaa gaa gtc agt ctt tct aag acg gtt atg     1440
Lys Gly Asp Ala Pro Glu Glu Glu Val Ser Leu Ser Lys Thr Val Met
        465                 470                 475 aaa ttt tgg gct aac ttc gcc cgt agt gga aac cct aat gga gaa gga     1488
Lys Phe Trp Ala Asn Phe Ala Arg Ser Gly Asn Pro Asn Gly Glu Gly
    480                 485                 490 ttg cct cac tgg ccg atg tac gat caa gag gag gga tac ctt caa att     1536
Leu Pro His Trp Pro Met Tyr Asp Gln Glu Glu Gly Tyr Leu Gln Ile
495                 500                 505                 510 ggt gtc aac act caa gca gct aag agg ttg aaa ggc gag gag gtt gct     1584
Gly Val Asn Thr Gln Ala Ala Lys Arg Leu Lys Gly Glu Glu Val Ala
                515                 520                 525 ttt tgg aac gac ctg ttg tcc aag gaa gca gca aag aag cca cct aag     1632
Phe Trp Asn Asp Leu Leu Ser Lys Glu Ala Ala Lys Lys Pro Pro Lys
            530                 535                 540 ata aag cac gcc gaa ttg taataagctt                                  1660
Ile Lys His Ala Glu Leu
```

545

<210> SEQ ID NO 6
<211> LENGTH: 548
<212> TYPE: PRT
<213> ORGANISM: Unknown
<220> FEATURE:
<223> OTHER INFORMATION: Synthetic Construct

<400> SEQUENCE: 6

```
Gly Gln Pro Ala Ser Pro Pro Val Val Asp Thr Ala Gln Gly Arg Val
1               5                   10                  15

Leu Gly Lys Tyr Val Ser Leu Glu Gly Leu Ala Gln Pro Val Ala Val
            20                  25                  30

Phe Leu Gly Val Pro Phe Ala Lys Pro Pro Leu Gly Ser Leu Arg Phe
        35                  40                  45

Ala Pro Pro Gln Pro Ala Glu Pro Trp Ser Phe Val Lys Asn Thr Thr
    50                  55                  60

Ser Tyr Pro Pro Met Cys Cys Gln Asp Pro Val Ala Gly Gln Met Thr
65                  70                  75                  80

Ser Asp Leu Phe Thr Asn Gly Lys Glu Arg Leu Ile Pro Glu Phe Ser
                85                  90                  95

Glu Asp Cys Leu Tyr Leu Asn Ile Tyr Thr Pro Ala Asp Leu Thr Lys
            100                 105                 110

Arg Gly Arg Leu Pro Val Met Val Trp Ile His Gly Gly Leu Val
        115                 120                 125

Val Gly Gly Ala Ser Thr Tyr Asp Gly Leu Ala Leu Ala Ala His Glu
    130                 135                 140

Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp
                165                 170                 175

Gln Val Ala Ala Leu His Trp Val Gln Glu Asn Ile Ala Asn Phe Gly
            180                 185                 190

Gly Asp Thr Gly Ser Val Thr Ile Phe Gly Glu Ser Ala Gly Gly Glu
        195                 200                 205

Ser Val Ser Val Leu Val Leu Ser Pro Leu Ala Lys Asn Leu Phe His
    210                 215                 220

Arg Ala Ile Ser Glu Ser Gly Val Ala Leu Thr Ala Gly Leu Val Arg
225                 230                 235                 240

Lys Asp Met Lys Ala Ala Ala Lys Gln Ile Ala Val Leu Ala Gly Cys
                245                 250                 255

Lys Thr Thr Thr Ser Ala Val Phe Val His Cys Leu Arg Gln Lys Ser
            260                 265                 270

Glu Asp Glu Leu Leu Asp Leu Thr Leu Lys Met Lys Phe Leu Thr Leu
        275                 280                 285

Asp Leu His Gly Asp Pro Arg Glu Ser His Pro Phe Leu Pro Thr Val
    290                 295                 300

Val Asp Gly Val Leu Leu Pro Lys Met Pro Glu Glu Ile Leu Ala Glu
305                 310                 315                 320

Lys Asp Phe Asn Thr Val Pro Tyr Ile Val Gly Ile Asn Lys Gln Glu
                325                 330                 335

Phe Gly Trp Leu Leu Pro Thr Met Met Gly Phe Pro Leu Ser Glu Gly
            340                 345                 350

Lys Leu Asp Gln Lys Thr Ala Thr Ser Leu Leu Trp Lys Ser Phe Pro
```

```
                    355                  360                  365
Ile Thr Asn Ile Pro Glu Glu Leu Thr Pro Val Ala Thr Asp Lys Tyr
    370                  375                  380
Leu Gly Gly Thr Asp Asp Pro Val Lys Lys Asp Leu Phe Leu Asp
385                  390                  395                  400
Leu Met Gly Asp Val Val Phe Gly Val Pro Ser Val Thr Val Ala Arg
                    405                  410                  415
Gln His Arg Asp Ala Gly Ala Pro Thr Tyr Met Tyr Glu Phe Gln Tyr
                420                  425                  430
Arg Pro Ser Phe Ser Ser Asp Lys Lys Pro Lys Thr Val Ile Gly Asp
            435                  440                  445
His Gly Asp Glu Ile Phe Ser Val Phe Gly Phe Pro Leu Leu Lys Gly
        450                  455                  460
Asp Ala Pro Glu Glu Val Ser Leu Ser Lys Thr Val Met Lys Phe
465                  470                  475                  480
Trp Ala Asn Phe Ala Arg Ser Gly Asn Pro Asn Gly Glu Gly Leu Pro
                485                  490                  495
His Trp Pro Met Tyr Asp Gln Glu Glu Gly Tyr Leu Gln Ile Gly Val
            500                  505                  510
Asn Thr Gln Ala Ala Lys Arg Leu Lys Gly Glu Val Ala Phe Trp
        515                  520                  525
Asn Asp Leu Leu Ser Lys Glu Ala Ala Lys Pro Pro Lys Ile Lys
530                  535                  540
His Ala Glu Leu
545

<210> SEQ ID NO 7
<211> LENGTH: 1660
<212> TYPE: DNA
<213> ORGANISM: Unknown
<220> FEATURE:
<223> OTHER INFORMATION: Synthetic gene
<220> FEATURE:
<221> NAME/KEY: exon
<222> LOCATION: (7)..(1650)
<223> OTHER INFORMATION: Pig Liver Esrterase 2
<220> FEATURE:
<221> NAME/KEY: CDS
<222> LOCATION: (7)..(1650)
<223> OTHER INFORMATION: Pig Liver Esrterase 2

<400> SEQUENCE: 7 catatg gga caa cca gct tcg ccg cct gtc gtt gat acc gct caa gga         48
       Gly Gln Pro Ala Ser Pro Pro Val Val Asp Thr Ala Gln Gly
        1               5                  10 cga gtc ttg ggt aag tac gtc tct tta gag gga ttg gca caa ccg gtt        96
Arg Val Leu Gly Lys Tyr Val Ser Leu Glu Gly Leu Ala Gln Pro Val
15                  20                  25                  30 gct gtc ttc ttg gga gtc cct ttt gct aag cca cct ctt gga tct ttg       144
Ala Val Phe Leu Gly Val Pro Phe Ala Lys Pro Pro Leu Gly Ser Leu
                35                  40                  45 agg ttt gcc ccg ccg caa cca gca gag cca tgg tct ttc gtt aag aac       192
Arg Phe Ala Pro Pro Gln Pro Ala Glu Pro Trp Ser Phe Val Lys Asn
            50                  55                  60 act act tcc tac cct cca atg tgt tgt caa gat cca gtc gta gaa caa       240
Thr Thr Ser Tyr Pro Pro Met Cys Cys Gln Asp Pro Val Val Glu Gln
        65                  70                  75 atg acg tca gac cta ttc act aac gga aag gaa agg ctt acc ctg gag       288
Met Thr Ser Asp Leu Phe Thr Asn Gly Lys Glu Arg Leu Thr Leu Glu
    80                  85                  90
```

-continued

| | | |
|---|---|---|
| ttc tct gag gat tgc ctt tac cta aat att tac act cct gcc gat ttg<br>Phe Ser Glu Asp Cys Leu Tyr Leu Asn Ile Tyr Thr Pro Ala Asp Leu<br>95                  100                 105                 110 | | 336 |
| aca aag agg ggt agg ttg ccg gtt atg gtt tgg att cat gga gga ggt<br>Thr Lys Arg Gly Arg Leu Pro Val Met Val Trp Ile His Gly Gly Gly<br>             115                 120                 125 | | 384 |
| ttg gtt ctg ggc gga gca ccg atg tat gac gga gtg gtt ctt gcc gcg<br>Leu Val Leu Gly Gly Ala Pro Met Tyr Asp Gly Val Val Leu Ala Ala<br>         130                 135                 140 | | 432 |
| cac gag aac gtt gtt gtt gtt gct att caa tac cgt ttg ggt att tgg<br>His Glu Asn Val Val Val Val Ala Ile Gln Tyr Arg Leu Gly Ile Trp<br>     145                 150                 155 | | 480 |
| gga ttt ttc tcc aca gga gat gag cat tcc cgt gga aac tgg ggc cat<br>Gly Phe Phe Ser Thr Gly Asp Glu His Ser Arg Gly Asn Trp Gly His<br> 160                 165                 170 | | 528 |
| tta gat caa gtt gct gca ttg cat tgg gtc caa gaa aac att gct aac<br>Leu Asp Gln Val Ala Ala Leu His Trp Val Gln Glu Asn Ile Ala Asn<br>175                 180                 185                 190 | | 576 |
| ttc gga ggt gat cca ggt tct gtt act att ttc gga gaa tca gca ggc<br>Phe Gly Gly Asp Pro Gly Ser Val Thr Ile Phe Gly Glu Ser Ala Gly<br>             195                 200                 205 | | 624 |
| gga gag agt gtc tct gta ttg gtt tta tca cca tta gct aag aac ctt<br>Gly Glu Ser Val Ser Val Leu Val Leu Ser Pro Leu Ala Lys Asn Leu<br>         210                 215                 220 | | 672 |
| ttt cat cgt gct att tcc gaa agt ggt gtt gct tta acc gtc gct ttg<br>Phe His Arg Ala Ile Ser Glu Ser Gly Val Ala Leu Thr Val Ala Leu<br>     225                 230                 235 | | 720 |
| gtc agg aag gat atg aag gcc gca gcc aag cag atc gct gtc ctt gca<br>Val Arg Lys Asp Met Lys Ala Ala Ala Lys Gln Ile Ala Val Leu Ala<br> 240                 245                 250 | | 768 |
| gga tgc aaa act act act tcg gca gtc ttc gtg cat tgt ttg cgt caa<br>Gly Cys Lys Thr Thr Thr Ser Ala Val Phe Val His Cys Leu Arg Gln<br>255                 260                 265                 270 | | 816 |
| aag tcg gaa gat gaa ctt tta gac ctc acg ttg aag atg aaa ttc ctg<br>Lys Ser Glu Asp Glu Leu Leu Asp Leu Thr Leu Lys Met Lys Phe Leu<br>             275                 280                 285 | | 864 |
| acc ctt gac ttt cac gga gat caa agg gaa tct cac cct ttt ttg ccg<br>Thr Leu Asp Phe His Gly Asp Gln Arg Glu Ser His Pro Phe Leu Pro<br>         290                 295                 300 | | 912 |
| act gtt gtt gac gga gtt ttg ttg cct aag atg cct gag gaa atc ttg<br>Thr Val Val Asp Gly Val Leu Leu Pro Lys Met Pro Glu Glu Ile Leu<br>     305                 310                 315 | | 960 |
| gcc gag aag gac ttt aac acc gtc cca tac att gtt gga att aac aag<br>Ala Glu Lys Asp Phe Asn Thr Val Pro Tyr Ile Val Gly Ile Asn Lys<br> 320                 325                 330 | | 1008 |
| cag gag ttc gga tgg ctt ttg cca acg atg atg gga ttt cct ctt tcc<br>Gln Glu Phe Gly Trp Leu Leu Pro Thr Met Met Gly Phe Pro Leu Ser<br>335                 340                 345                 350 | | 1056 |
| gag gga aag ttg gat caa aag acg gct acg tca ctt ttg tgg aag tcc<br>Glu Gly Lys Leu Asp Gln Lys Thr Ala Thr Ser Leu Leu Trp Lys Ser<br>             355                 360                 365 | | 1104 |
| tac cca att gcc aac att cct gaa gag ttg acc cca gtt gct acc gat<br>Tyr Pro Ile Ala Asn Ile Pro Glu Glu Leu Thr Pro Val Ala Thr Asp<br>         370                 375                 380 | | 1152 |
| aag tat tta gga gga aca gat gat cct gtc aaa aag aaa gat ttg ttt<br>Lys Tyr Leu Gly Gly Thr Asp Asp Pro Val Lys Lys Lys Asp Leu Phe<br>     385                 390                 395 | | 1200 |
| ttg gat ctg atg gga gac gtt gtt ttc ggc gtc cca tca gtt acg gtt<br>Leu Asp Leu Met Gly Asp Val Val Phe Gly Val Pro Ser Val Thr Val | | 1248 |

| | | | | | | | | | | | | | | | |
|---|---|---|---|---|---|---|---|---|---|---|---|---|---|---|---|
| | | | 400 | | | | 405 | | | | 410 | | | | |
| gct | cgt | cag | cat | agg | gac | gca | gga | gct | cca | act | tac | atg | tat | gag | ttc |
| Ala | Arg | Gln | His | Arg | Asp | Ala | Gly | Ala | Pro | Thr | Tyr | Met | Tyr | Glu | Phe |
| 415 | | | | 420 | | | | | 425 | | | | | 430 | |

1296

| caa | tat | cgt | cca | tct | ttt | tca | tcg | gat | aag | aaa | cct | aag | acg | gtt | att |
|---|---|---|---|---|---|---|---|---|---|---|---|---|---|---|---|
| Gln | Tyr | Arg | Pro | Ser | Phe | Ser | Ser | Asp | Lys | Lys | Pro | Lys | Thr | Val | Ile |
| | | | | 435 | | | | | 440 | | | | | 445 | |

1344

| gga | gat | cat | gga | gac | gaa | att | ttt | tcc | gtc | ttc | ggc | gcc | cca | ttc | ctc |
|---|---|---|---|---|---|---|---|---|---|---|---|---|---|---|---|
| Gly | Asp | His | Gly | Asp | Glu | Ile | Phe | Ser | Val | Phe | Gly | Ala | Pro | Phe | Leu |
| | | | 450 | | | | | 455 | | | | | 460 | | |

1392

| aga | ggt | gac | gct | cca | gag | gaa | gaa | gtc | agt | ctt | tct | aag | acg | gtt | atg |
|---|---|---|---|---|---|---|---|---|---|---|---|---|---|---|---|
| Arg | Gly | Asp | Ala | Pro | Glu | Glu | Glu | Val | Ser | Leu | Ser | Lys | Thr | Val | Met |
| | | | 465 | | | | 470 | | | | | 475 | | | |

1440

| aaa | ttt | tgg | gct | aac | ttc | gcc | cgt | agt | gga | aac | cct | aat | gga | gaa | gga |
|---|---|---|---|---|---|---|---|---|---|---|---|---|---|---|---|
| Lys | Phe | Trp | Ala | Asn | Phe | Ala | Arg | Ser | Gly | Asn | Pro | Asn | Gly | Glu | Gly |
| 480 | | | | | 485 | | | | | 490 | | | | | |

1488

| ttg | cct | cac | tgg | ccg | atg | tac | gat | caa | gag | gag | gga | tac | ctt | caa | att |
|---|---|---|---|---|---|---|---|---|---|---|---|---|---|---|---|
| Leu | Pro | His | Trp | Pro | Met | Tyr | Asp | Gln | Glu | Glu | Gly | Tyr | Leu | Gln | Ile |
| 495 | | | | 500 | | | | | 505 | | | | | 510 | |

1536

| ggt | gtc | aac | act | caa | gca | gct | aag | agg | ttg | aaa | ggc | gag | gag | gtt | gct |
|---|---|---|---|---|---|---|---|---|---|---|---|---|---|---|---|
| Gly | Val | Asn | Thr | Gln | Ala | Ala | Lys | Arg | Leu | Lys | Gly | Glu | Glu | Val | Ala |
| | | | | 515 | | | | | 520 | | | | | 525 | |

1584

| ttt | tgg | aac | gac | ctg | ttg | tcc | aag | gaa | gca | gca | aag | aag | cca | cct | aag |
|---|---|---|---|---|---|---|---|---|---|---|---|---|---|---|---|
| Phe | Trp | Asn | Asp | Leu | Leu | Ser | Lys | Glu | Ala | Ala | Lys | Lys | Pro | Pro | Lys |
| | | | 530 | | | | | 535 | | | | | 540 | | |

1632

| ata | aag | cac | gcc | gaa | ttg | taataagctt |
|---|---|---|---|---|---|---|
| Ile | Lys | His | Ala | Glu | Leu | |
| | | 545 | | | | |

1660

<210> SEQ ID NO 8
<211> LENGTH: 548
<212> TYPE: PRT
<213> ORGANISM: Unknown
<220> FEATURE:
<223> OTHER INFORMATION: Synthetic Construct

<400> SEQUENCE: 8

Gly Gln Pro Ala Ser Pro Pro Val Val Asp Thr Ala Gln Gly Arg Val
1               5                   10                  15

Leu Gly Lys Tyr Val Ser Leu Glu Gly Leu Ala Gln Pro Val Ala Val
            20                  25                  30

Phe Leu Gly Val Pro Phe Ala Lys Pro Pro Leu Gly Ser Leu Arg Phe
        35                  40                  45

Ala Pro Pro Gln Pro Ala Glu Pro Trp Ser Phe Val Lys Asn Thr Thr
    50                  55                  60

Ser Tyr Pro Pro Met Cys Cys Gln Asp Pro Val Val Glu Gln Met Thr
65                  70                  75                  80

Ser Asp Leu Phe Thr Asn Gly Lys Glu Arg Leu Thr Leu Glu Phe Ser
                85                  90                  95

Glu Asp Cys Leu Tyr Leu Asn Ile Tyr Thr Pro Ala Asp Leu Thr Lys
            100                 105                 110

Arg Gly Arg Leu Pro Val Met Val Trp Ile His Gly Gly Gly Leu Val
        115                 120                 125

Leu Gly Gly Ala Pro Met Tyr Asp Gly Val Val Leu Ala Ala His Glu
    130                 135                 140

Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp

```
            165                 170                 175
Gln Val Ala Ala Leu His Trp Val Gln Glu Asn Ile Ala Asn Phe Gly
            180                 185                 190

Gly Asp Pro Gly Ser Val Thr Ile Phe Gly Glu Ser Ala Gly Gly Glu
            195                 200                 205

Ser Val Ser Val Leu Val Leu Ser Pro Leu Ala Lys Asn Leu Phe His
210                 215                 220

Arg Ala Ile Ser Glu Ser Gly Val Ala Leu Thr Val Ala Leu Val Arg
225                 230                 235                 240

Lys Asp Met Lys Ala Ala Lys Gln Ile Ala Val Leu Ala Gly Cys
            245                 250                 255

Lys Thr Thr Thr Ser Ala Val Phe Val His Cys Leu Arg Gln Lys Ser
            260                 265                 270

Glu Asp Glu Leu Leu Asp Leu Thr Leu Lys Met Lys Phe Leu Thr Leu
            275                 280                 285

Asp Phe His Gly Asp Gln Arg Glu Ser His Pro Phe Leu Pro Thr Val
            290                 295                 300

Val Asp Gly Val Leu Leu Pro Lys Met Pro Glu Glu Ile Leu Ala Glu
305                 310                 315                 320

Lys Asp Phe Asn Thr Val Pro Tyr Ile Val Gly Ile Asn Lys Gln Glu
            325                 330                 335

Phe Gly Trp Leu Leu Pro Thr Met Met Gly Phe Pro Leu Ser Glu Gly
            340                 345                 350

Lys Leu Asp Gln Lys Thr Ala Thr Ser Leu Leu Trp Lys Ser Tyr Pro
            355                 360                 365

Ile Ala Asn Ile Pro Glu Glu Leu Thr Pro Val Ala Thr Asp Lys Tyr
            370                 375                 380

Leu Gly Gly Thr Asp Asp Pro Val Lys Lys Asp Leu Phe Leu Asp
385                 390                 395                 400

Leu Met Gly Asp Val Val Phe Gly Val Pro Ser Val Thr Val Ala Arg
            405                 410                 415

Gln His Arg Asp Ala Gly Ala Pro Thr Tyr Met Tyr Glu Phe Gln Tyr
            420                 425                 430

Arg Pro Ser Phe Ser Ser Asp Lys Lys Pro Lys Thr Val Ile Gly Asp
            435                 440                 445

His Gly Asp Glu Ile Phe Ser Val Phe Gly Ala Pro Phe Leu Arg Gly
            450                 455                 460

Asp Ala Pro Glu Glu Glu Val Ser Leu Ser Lys Thr Val Met Lys Phe
465                 470                 475                 480

Trp Ala Asn Phe Ala Arg Ser Gly Asn Pro Asn Gly Glu Gly Leu Pro
            485                 490                 495

His Trp Pro Met Tyr Asp Gln Glu Glu Gly Tyr Leu Gln Ile Gly Val
            500                 505                 510

Asn Thr Gln Ala Ala Lys Arg Leu Lys Gly Glu Glu Val Ala Phe Trp
            515                 520                 525

Asn Asp Leu Leu Ser Lys Glu Ala Ala Lys Lys Pro Pro Lys Ile Lys
            530                 535                 540

His Ala Glu Leu
545

<210> SEQ ID NO 9
<211> LENGTH: 1660
<212> TYPE: DNA
<213> ORGANISM: Unknown
```

```
<220> FEATURE:
<223> OTHER INFORMATION: Synthetic gene
<220> FEATURE:
<221> NAME/KEY: exon
<222> LOCATION: (7)..(1650)
<223> OTHER INFORMATION: Pig Liver Esterase 3
<220> FEATURE:
<221> NAME/KEY: CDS
<222> LOCATION: (7)..(1650)
<223> OTHER INFORMATION: Pig Liver Esterase 3

<400> SEQUENCE: 9 catatg gga caa cca gct tcg ccg cct gtc gtt gat acc gct caa gga        48
       Gly Gln Pro Ala Ser Pro Pro Val Val Asp Thr Ala Gln Gly
       1               5                   10 cga gtc ttg ggt aag tac gtc tct tta gag gga ttg gca caa ccg gtt       96
Arg Val Leu Gly Lys Tyr Val Ser Leu Glu Gly Leu Ala Gln Pro Val
15                  20                  25                  30 gct gtc ttc ttg gga gtc cct ttt gct aag cca cct ctt gga tct ttg      144
Ala Val Phe Leu Gly Val Pro Phe Ala Lys Pro Pro Leu Gly Ser Leu
                35                  40                  45 agg ttt gcc ccg ccg caa cca gca gag cca tgg tct ttc gtt aag aac      192
Arg Phe Ala Pro Pro Gln Pro Ala Glu Pro Trp Ser Phe Val Lys Asn
            50                  55                  60 act act tcc tac cct cca atg tgt tgt caa gaa cca atc gga gga caa      240
Thr Thr Ser Tyr Pro Pro Met Cys Cys Gln Glu Pro Ile Gly Gly Gln
65                  70                  75 atg ctt tca gac cta ttc act aac aga aag gaa agg ctt atc ccg gag      288
Met Leu Ser Asp Leu Phe Thr Asn Arg Lys Glu Arg Leu Ile Pro Glu
        80                  85                  90 ttc tct gag gat tgc ctt tac cta aat att tac act cct gcc gat ttg      336
Phe Ser Glu Asp Cys Leu Tyr Leu Asn Ile Tyr Thr Pro Ala Asp Leu
95                  100                 105                 110 aca aag agg ggt agg ttg ccg gtt atg gtt tgg att cat gga gga ggt      384
Thr Lys Arg Gly Arg Leu Pro Val Met Val Trp Ile His Gly Gly Gly
                115                 120                 125 ttg gtt gtt ggc gga gca tcc act tat gac gga ttg gct ctt gcc gcg      432
Leu Val Val Gly Gly Ala Ser Thr Tyr Asp Gly Leu Ala Leu Ala Ala
            130                 135                 140 cac gag aac gtt gtt gtt gtt gct att caa tac cgt ttg ggt att tgg      480
His Glu Asn Val Val Val Val Ala Ile Gln Tyr Arg Leu Gly Ile Trp
        145                 150                 155 gga ttt ttc tcc aca gga gat gag cat tcc cgt gga aac tgg ggc cat      528
Gly Phe Phe Ser Thr Gly Asp Glu His Ser Arg Gly Asn Trp Gly His
        160                 165                 170 tta gat caa gtt gct gca ttg cat tgg gtc caa gaa aac att gct aac      576
Leu Asp Gln Val Ala Ala Leu His Trp Val Gln Glu Asn Ile Ala Asn
175                 180                 185                 190 ttc gga ggt gat cca ggt tct gtt act att ttc gga gaa tca gca ggc      624
Phe Gly Gly Asp Pro Gly Ser Val Thr Ile Phe Gly Glu Ser Ala Gly
                195                 200                 205 gga gag agt gtc tct gta ttg gtt tta tca cca tta gct aag aac ctt      672
Gly Glu Ser Val Ser Val Leu Val Leu Ser Pro Leu Ala Lys Asn Leu
            210                 215                 220 ttt cat cgt gct att tcc gaa agt ggt gtt gct ttt acc gcc ggt ttg      720
Phe His Arg Ala Ile Ser Glu Ser Gly Val Ala Phe Thr Ala Gly Leu
        225                 230                 235 gtc agg aag gat atg aag gcc gca gcc aag cag atc gct gtc ctt gca      768
Val Arg Lys Asp Met Lys Ala Ala Ala Lys Gln Ile Ala Val Leu Ala
240                 245                 250 gga tgc aaa act act act tcg gca gtc ttc gtg cat tgt ttg cgt caa      816
Gly Cys Lys Thr Thr Thr Ser Ala Val Phe Val His Cys Leu Arg Gln
```

```
                255                 260                 265                 270
aag tcg gaa gat gaa ctt tta gac ctc acg ttg aag atg aaa ccc tta         864
Lys Ser Glu Asp Glu Leu Leu Asp Leu Thr Leu Lys Met Lys Pro Leu
                    275                 280                 285 acc ctt gac tta cac gga gat cca agg gaa tct cac cct ttt ttg acc         912
Thr Leu Asp Leu His Gly Asp Pro Arg Glu Ser His Pro Phe Leu Thr
                    290                 295                 300 act gtt gtt gac gga gtt ttg ttg cct aag atg cct gag gaa atc ttg         960
Thr Val Val Asp Gly Val Leu Leu Pro Lys Met Pro Glu Glu Ile Leu
                    305                 310                 315 gcc gag aag gac ttt aac acc gtc cca tac att gtt gga att aac aag        1008
Ala Glu Lys Asp Phe Asn Thr Val Pro Tyr Ile Val Gly Ile Asn Lys
320                 325                 330 cag gag ttc gga tgg ctt ttg cca acg atg atg gga ttt cct ctt tcc        1056
Gln Glu Phe Gly Trp Leu Leu Pro Thr Met Met Gly Phe Pro Leu Ser
335                 340                 345                 350 gag gga aag ttg gat caa aag acg gct acg tca ctt ttg tgg aag tcc        1104
Glu Gly Lys Leu Asp Gln Lys Thr Ala Thr Ser Leu Leu Trp Lys Ser
                    355                 360                 365 tac cca att gcc aac att cct gaa gag ttg acc cca gtt gct acc gat        1152
Tyr Pro Ile Ala Asn Ile Pro Glu Glu Leu Thr Pro Val Ala Thr Asp
                    370                 375                 380 aag tat tta gga gga aca gat gat cct gtc aaa aag aaa gat ttg ttt        1200
Lys Tyr Leu Gly Gly Thr Asp Asp Pro Val Lys Lys Lys Asp Leu Phe
                    385                 390                 395 ttg gat ctg atg gga gac gtt gtt ttc ggc gtc cca tca gtt acg gtt        1248
Leu Asp Leu Met Gly Asp Val Val Phe Gly Val Pro Ser Val Thr Val
400                 405                 410 gct cgt cag cat agg gac gca gga gct cca act tac atg tat gag ttc        1296
Ala Arg Gln His Arg Asp Ala Gly Ala Pro Thr Tyr Met Tyr Glu Phe
415                 420                 425                 430 caa tat cgt cca tct ttt tca tcg gat aag aaa cct aag acg gtt att        1344
Gln Tyr Arg Pro Ser Phe Ser Ser Asp Lys Lys Pro Lys Thr Val Ile
                    435                 440                 445 gga gat cat gga gac gaa att ttt tcc gtc ttc ggc ttc cca ttg ctc        1392
Gly Asp His Gly Asp Glu Ile Phe Ser Val Phe Gly Phe Pro Leu Leu
                    450                 455                 460 aaa ggt gac gct cca gag gaa gaa gtc agt ctt tct aag acg gtt atg        1440
Lys Gly Asp Ala Pro Glu Glu Glu Val Ser Leu Ser Lys Thr Val Met
465                 470                 475 aaa ttt tgg gct aac ttc gcc cgt agt gga aac cct aat gga gaa gga        1488
Lys Phe Trp Ala Asn Phe Ala Arg Ser Gly Asn Pro Asn Gly Glu Gly
        480                 485                 490 ttg cct cac tgg ccg atg tac gat caa gag gag gga tac ctt caa att        1536
Leu Pro His Trp Pro Met Tyr Asp Gln Glu Glu Gly Tyr Leu Gln Ile
495                 500                 505                 510 ggt gtc aac act caa gca gct aag agg ttg aaa ggc gag gag gtt gct        1584
Gly Val Asn Thr Gln Ala Ala Lys Arg Leu Lys Gly Glu Glu Val Ala
                    515                 520                 525 ttt tgg aac gac ctg ttg tcc aag gaa gca gca aag aag cca cct aag        1632
Phe Trp Asn Asp Leu Leu Ser Lys Glu Ala Ala Lys Lys Pro Pro Lys
                    530                 535                 540 ata aag cac gcc gaa ttg taataagctt                                      1660
Ile Lys His Ala Glu Leu
                    545

<210> SEQ ID NO 10
<211> LENGTH: 548
<212> TYPE: PRT
<213> ORGANISM: Unknown
```

<220> FEATURE:
<223> OTHER INFORMATION: Synthetic Construct

<400> SEQUENCE: 10

```
Gly Gln Pro Ala Ser Pro Pro Val Val Asp Thr Ala Gln Gly Arg Val
1               5                   10                  15

Leu Gly Lys Tyr Val Ser Leu Glu Gly Leu Ala Gln Pro Val Ala Val
            20                  25                  30

Phe Leu Gly Val Pro Phe Ala Lys Pro Pro Leu Gly Ser Leu Arg Phe
        35                  40                  45

Ala Pro Pro Gln Pro Ala Glu Pro Trp Ser Phe Val Lys Asn Thr Thr
50                  55                  60

Ser Tyr Pro Pro Met Cys Cys Gln Glu Pro Ile Gly Gly Gln Met Leu
65                  70                  75                  80

Ser Asp Leu Phe Thr Asn Arg Lys Glu Arg Leu Ile Pro Glu Phe Ser
                85                  90                  95

Glu Asp Cys Leu Tyr Leu Asn Ile Tyr Thr Pro Ala Asp Leu Thr Lys
            100                 105                 110

Arg Gly Arg Leu Pro Val Met Val Trp Ile His Gly Gly Gly Leu Val
        115                 120                 125

Val Gly Gly Ala Ser Thr Tyr Asp Gly Leu Ala Leu Ala Ala His Glu
130                 135                 140

Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp
                165                 170                 175

Gln Val Ala Ala Leu His Trp Val Gln Glu Asn Ile Ala Asn Phe Gly
            180                 185                 190

Gly Asp Pro Gly Ser Val Thr Ile Phe Gly Glu Ser Ala Gly Gly Glu
        195                 200                 205

Ser Val Ser Val Leu Val Leu Ser Pro Leu Ala Lys Asn Leu Phe His
210                 215                 220

Arg Ala Ile Ser Glu Ser Gly Val Ala Phe Thr Ala Gly Leu Val Arg
225                 230                 235                 240

Lys Asp Met Lys Ala Ala Lys Gln Ile Ala Val Leu Ala Gly Cys
                245                 250                 255

Lys Thr Thr Thr Ser Ala Val Phe Val His Cys Leu Arg Gln Lys Ser
            260                 265                 270

Glu Asp Glu Leu Leu Asp Leu Thr Leu Lys Met Lys Pro Leu Thr Leu
        275                 280                 285

Asp Leu His Gly Asp Pro Arg Glu Ser His Pro Phe Leu Thr Thr Val
290                 295                 300

Val Asp Gly Val Leu Leu Pro Lys Met Pro Glu Ile Leu Ala Glu
305                 310                 315                 320

Lys Asp Phe Asn Thr Val Pro Tyr Ile Val Gly Ile Asn Lys Gln Glu
                325                 330                 335

Phe Gly Trp Leu Leu Pro Thr Met Met Gly Phe Pro Leu Ser Glu Gly
            340                 345                 350

Lys Leu Asp Gln Lys Thr Ala Ser Leu Leu Trp Lys Ser Tyr Pro
        355                 360                 365

Ile Ala Asn Ile Pro Glu Glu Leu Thr Pro Val Ala Thr Asp Lys Tyr
370                 375                 380

Leu Gly Gly Thr Asp Asp Pro Val Lys Lys Lys Asp Leu Phe Leu Asp
385                 390                 395                 400
```

```
Leu Met Gly Asp Val Val Phe Gly Val Pro Ser Val Thr Val Ala Arg
            405                 410                 415

Gln His Arg Asp Ala Gly Ala Pro Thr Tyr Met Tyr Glu Phe Gln Tyr
        420                 425                 430

Arg Pro Ser Phe Ser Ser Asp Lys Lys Pro Lys Thr Val Ile Gly Asp
            435                 440                 445

His Gly Asp Glu Ile Phe Ser Val Phe Gly Phe Pro Leu Leu Lys Gly
        450                 455                 460

Asp Ala Pro Glu Glu Glu Val Ser Leu Ser Lys Thr Val Met Lys Phe
465                 470                 475                 480

Trp Ala Asn Phe Ala Arg Ser Gly Asn Pro Asn Gly Glu Gly Leu Pro
            485                 490                 495

His Trp Pro Met Tyr Asp Gln Glu Glu Gly Tyr Leu Gln Ile Gly Val
            500                 505                 510

Asn Thr Gln Ala Ala Lys Arg Leu Lys Gly Glu Glu Val Ala Phe Trp
            515                 520                 525

Asn Asp Leu Leu Ser Lys Glu Ala Ala Lys Lys Pro Lys Ile Lys
            530                 535                 540

His Ala Glu Leu
545

<210> SEQ ID NO 11
<211> LENGTH: 1660
<212> TYPE: DNA
<213> ORGANISM: Unknown
<220> FEATURE:
<223> OTHER INFORMATION: Synthetic gene
<220> FEATURE:
<221> NAME/KEY: exon
<222> LOCATION: (7)..(1650)
<223> OTHER INFORMATION: Pig Liver Esterase 4
<220> FEATURE:
<221> NAME/KEY: CDS
<222> LOCATION: (7)..(1650)
<223> OTHER INFORMATION: Pig Liver Esterase 4

<400> SEQUENCE: 11 catatg gga caa cca gct tcg ccg cct gtc gtt gat acc gct caa gga        48
       Gly Gln Pro Ala Ser Pro Pro Val Val Asp Thr Ala Gln Gly
        1               5                   10 cga gtc ttg ggt aag tac gtc tct tta gag gga ttg gca caa ccg gtt       96
Arg Val Leu Gly Lys Tyr Val Ser Leu Glu Gly Leu Ala Gln Pro Val
15                  20                  25                  30 gct gtc ttc ttg gga gtc cct ttt gct aag cca cct ctt gga tct ttg      144
Ala Val Phe Leu Gly Val Pro Phe Ala Lys Pro Pro Leu Gly Ser Leu
                35                  40                  45 agg ttt gcc ccg ccg caa cca gca gag cca tgg tct ttc gtt aag aac      192
Arg Phe Ala Pro Pro Gln Pro Ala Glu Pro Trp Ser Phe Val Lys Asn
            50                  55                  60 act act tcc tac cct cca atg tgt tgt caa gat cca gtc gca gga caa      240
Thr Thr Ser Tyr Pro Pro Met Cys Cys Gln Asp Pro Val Ala Gly Gln
        65                  70                  75 atg acg tca gac cta ttc act aac gga aag gaa agg ctt atc ccg gag      288
Met Thr Ser Asp Leu Phe Thr Asn Gly Lys Glu Arg Leu Ile Pro Glu
    80                  85                  90 ttc tct gag gat tgc ctt tac cta aat att tac act cct gcc gat ttg      336
Phe Ser Glu Asp Cys Leu Tyr Leu Asn Ile Tyr Thr Pro Ala Asp Leu
95                  100                 105                 110 aca aag agg ggt agg ttg ccg gtt atg gtt tgg att cat gga gga ggt      384
Thr Lys Arg Gly Arg Leu Pro Val Met Val Trp Ile His Gly Gly Gly
```

-continued

|  | 115 | 120 | 125 |  |
|---|---|---|---|---|
| ttg gtt gtt ggc gga gca tcc act tat gac gga ttg gct ctt gcc gcg<br>Leu Val Val Gly Gly Ala Ser Thr Tyr Asp Gly Leu Ala Leu Ala Ala<br>130 135 140 | | | | 432 |
| cac gag aac gtt gtt gtt gtt gct att caa tac cgt ttg ggt att tgg<br>His Glu Asn Val Val Val Val Ala Ile Gln Tyr Arg Leu Gly Ile Trp<br>145 150 155 | | | | 480 |
| gga ttt ttc tcc aca gga gat gag cat tcc cgt gga aac tgg ggc cat<br>Gly Phe Phe Ser Thr Gly Asp Glu His Ser Arg Gly Asn Trp Gly His<br>160 165 170 | | | | 528 |
| tta gat caa gtt gct gca ttg cat tgg gtc caa gaa aac att gct aac<br>Leu Asp Gln Val Ala Ala Leu His Trp Val Gln Glu Asn Ile Ala Asn<br>175 180 185 190 | | | | 576 |
| ttc gga ggt gat cca ggt tct gtt act att ttc gga gaa tca gca ggc<br>Phe Gly Gly Asp Pro Gly Ser Val Thr Ile Phe Gly Glu Ser Ala Gly<br>195 200 205 | | | | 624 |
| gga gag agt gtc tct gta ttg gtt tta tca cca tta gct aag aac ctt<br>Gly Glu Ser Val Ser Val Leu Val Leu Ser Pro Leu Ala Lys Asn Leu<br>210 215 220 | | | | 672 |
| ttt cat cgt gct att tcc gaa agt ggt gtt gct ttt acc gcc ggt ttg<br>Phe His Arg Ala Ile Ser Glu Ser Gly Val Ala Phe Thr Ala Gly Leu<br>225 230 235 | | | | 720 |
| gtc agg aag gat atg aag gcc gca gcc aag cag atc gct gtc ctt gca<br>Val Arg Lys Asp Met Lys Ala Ala Ala Lys Gln Ile Ala Val Leu Ala<br>240 245 250 | | | | 768 |
| gga tgc aaa act act act tcg gca gtc ttc gtg cat tgt ttg cgt caa<br>Gly Cys Lys Thr Thr Thr Ser Ala Val Phe Val His Cys Leu Arg Gln<br>255 260 265 270 | | | | 816 |
| aag tcg gaa gat gaa ctt tta gac ctc acg ttg aag atg aaa ccc tta<br>Lys Ser Glu Asp Glu Leu Leu Asp Leu Thr Leu Lys Met Lys Pro Leu<br>275 280 285 | | | | 864 |
| acc ctt gac tta cac gga gat cca agg gaa tct cac cct ttt ttg acc<br>Thr Leu Asp Leu His Gly Asp Pro Arg Glu Ser His Pro Phe Leu Thr<br>290 295 300 | | | | 912 |
| act gtt gtt gac gga gtt ttg ttg cct aag atg cct gag gaa atc ttg<br>Thr Val Val Asp Gly Val Leu Leu Pro Lys Met Pro Glu Glu Ile Leu<br>305 310 315 | | | | 960 |
| gcc gag aag gac ttt aac acc gtc cca tac att gtt gga att aac aag<br>Ala Glu Lys Asp Phe Asn Thr Val Pro Tyr Ile Val Gly Ile Asn Lys<br>320 325 330 | | | | 1008 |
| cag gag ttc gga tgg ctt ttg cca acg atg atg gga ttt cct ctt tcc<br>Gln Glu Phe Gly Trp Leu Leu Pro Thr Met Met Gly Phe Pro Leu Ser<br>335 340 345 350 | | | | 1056 |
| gag gga aag ttg gat caa aag acg gct acg tca ctt tgg aag tcc<br>Glu Gly Lys Leu Asp Gln Lys Thr Ala Thr Ser Leu Leu Trp Lys Ser<br>355 360 365 | | | | 1104 |
| tac cca att gcc aac att cct gaa gag ttg acc cca gtt gct acc gat<br>Tyr Pro Ile Ala Asn Ile Pro Glu Glu Leu Thr Pro Val Ala Thr Asp<br>370 375 380 | | | | 1152 |
| aag tat tta gga gga aca gat gat cct gtc aaa aag aaa gat ttg ttt<br>Lys Tyr Leu Gly Gly Thr Asp Asp Pro Val Lys Lys Lys Asp Leu Phe<br>385 390 395 | | | | 1200 |
| ttg gat ctg atg gga gac gtt gtt ttc ggc gtc cca tca gtt acg gtt<br>Leu Asp Leu Met Gly Asp Val Val Phe Gly Val Pro Ser Val Thr Val<br>400 405 410 | | | | 1248 |
| gct cgt cag cat agg gac gca gga gct cca act tac atg tat gag ttc<br>Ala Arg Gln His Arg Asp Ala Gly Ala Pro Thr Tyr Met Tyr Glu Phe<br>415 420 425 430 | | | | 1296 |
| caa tat cgt cca tct ttt tca tcg gat aag aaa cct aag acg gtt att | | | | 1344 |

```
                Gln Tyr Arg Pro Ser Phe Ser Asp Lys Lys Pro Lys Thr Val Ile
                                    435                 440                 445 gga gat cat gga gac gaa att ttt tcc gtc ttc ggc gcc cca ttc ctc              1392
Gly Asp His Gly Asp Glu Ile Phe Ser Val Phe Gly Ala Pro Phe Leu
            450                 455                 460 aga ggt gac gct cca gag gaa gaa gtc agt ctt tct aag acg gtt atg              1440
Arg Gly Asp Ala Pro Glu Glu Glu Val Ser Leu Ser Lys Thr Val Met
            465                 470                 475 aaa ttt tgg gct aac ttc gcc cgt agt gga aac cct aat gga gaa gga              1488
Lys Phe Trp Ala Asn Phe Ala Arg Ser Gly Asn Pro Asn Gly Glu Gly
        480                 485                 490 ttg cct cac tgg ccg atg tac gat caa gag gag gga tac ctt caa att              1536
Leu Pro His Trp Pro Met Tyr Asp Gln Glu Glu Gly Tyr Leu Gln Ile
495                 500                 505                 510 ggt gtc aac act caa gca gct aag agg ttg aaa ggc gag gag gtt gct              1584
Gly Val Asn Thr Gln Ala Ala Lys Arg Leu Lys Gly Glu Glu Val Ala
                515                 520                 525 ttt tgg aac gac ctg ttg tcc aag gaa gca gca aag aag cca cct aag              1632
Phe Trp Asn Asp Leu Leu Ser Lys Glu Ala Ala Lys Lys Pro Pro Lys
            530                 535                 540 ata aag cac gcc gaa ttg taataagctt                                           1660
Ile Lys His Ala Glu Leu
            545

<210> SEQ ID NO 12
<211> LENGTH: 548
<212> TYPE: PRT
<213> ORGANISM: Unknown
<220> FEATURE:
<223> OTHER INFORMATION: Synthetic Construct

<400> SEQUENCE: 12

Gly Gln Pro Ala Ser Pro Pro Val Val Asp Thr Ala Gln Gly Arg Val
1               5                   10                  15

Leu Gly Lys Tyr Val Ser Leu Glu Gly Leu Ala Gln Pro Val Ala Val
            20                  25                  30

Phe Leu Gly Val Pro Phe Ala Lys Pro Pro Leu Gly Ser Leu Arg Phe
        35                  40                  45

Ala Pro Pro Gln Pro Ala Glu Pro Trp Ser Phe Val Lys Asn Thr Thr
    50                  55                  60

Ser Tyr Pro Pro Met Cys Cys Gln Asp Pro Val Ala Gly Gln Met Thr
65                  70                  75                  80

Ser Asp Leu Phe Thr Asn Gly Lys Glu Arg Leu Ile Pro Glu Phe Ser
                85                  90                  95

Glu Asp Cys Leu Tyr Leu Asn Ile Tyr Thr Pro Ala Asp Leu Thr Lys
            100                 105                 110

Arg Gly Arg Leu Pro Val Met Val Trp Ile His Gly Gly Gly Leu Val
        115                 120                 125

Val Gly Gly Ala Ser Thr Tyr Asp Gly Leu Ala Leu Ala Ala His Glu
    130                 135                 140

Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp
                165                 170                 175

Gln Val Ala Ala Leu His Trp Val Gln Glu Asn Ile Ala Asn Phe Gly
            180                 185                 190

Gly Asp Pro Gly Ser Val Thr Ile Phe Gly Glu Ser Ala Gly Gly Glu
        195                 200                 205
```

Ser Val Ser Val Leu Val Leu Ser Pro Leu Ala Lys Asn Leu Phe His
210                 215                 220

Arg Ala Ile Ser Glu Ser Gly Val Ala Phe Thr Ala Gly Leu Val Arg
225                 230                 235                 240

Lys Asp Met Lys Ala Ala Lys Gln Ile Ala Val Leu Ala Gly Cys
            245                 250                 255

Lys Thr Thr Thr Ser Ala Val Phe Val His Cys Leu Arg Gln Lys Ser
                260                 265                 270

Glu Asp Glu Leu Leu Asp Leu Thr Leu Lys Met Lys Pro Leu Thr Leu
            275                 280                 285

Asp Leu His Gly Asp Pro Arg Glu Ser His Pro Phe Leu Thr Thr Val
            290                 295                 300

Val Asp Gly Val Leu Leu Pro Lys Met Pro Glu Glu Ile Leu Ala Glu
305                 310                 315                 320

Lys Asp Phe Asn Thr Val Pro Tyr Ile Val Gly Ile Asn Lys Gln Glu
                325                 330                 335

Phe Gly Trp Leu Leu Pro Thr Met Met Gly Phe Pro Leu Ser Glu Gly
            340                 345                 350

Lys Leu Asp Gln Lys Thr Ala Thr Ser Leu Leu Trp Lys Ser Tyr Pro
355                 360                 365

Ile Ala Asn Ile Pro Glu Glu Leu Thr Pro Val Ala Thr Asp Lys Tyr
370                 375                 380

Leu Gly Gly Thr Asp Asp Pro Val Lys Lys Asp Leu Phe Leu Asp
385                 390                 395                 400

Leu Met Gly Asp Val Val Phe Gly Val Pro Ser Val Thr Val Ala Arg
                405                 410                 415

Gln His Arg Asp Ala Gly Ala Pro Thr Tyr Met Tyr Glu Phe Gln Tyr
            420                 425                 430

Arg Pro Ser Phe Ser Ser Asp Lys Lys Pro Lys Thr Val Ile Gly Asp
            435                 440                 445

His Gly Asp Glu Ile Phe Ser Val Phe Gly Ala Pro Phe Leu Arg Gly
            450                 455                 460

Asp Ala Pro Glu Glu Glu Val Ser Leu Ser Lys Thr Val Met Lys Phe
465                 470                 475                 480

Trp Ala Asn Phe Ala Arg Ser Gly Asn Pro Asn Gly Glu Gly Leu Pro
                485                 490                 495

His Trp Pro Met Tyr Asp Gln Glu Glu Gly Tyr Leu Gln Ile Gly Val
            500                 505                 510

Asn Thr Gln Ala Ala Lys Arg Leu Lys Gly Glu Glu Val Ala Phe Trp
            515                 520                 525

Asn Asp Leu Leu Ser Lys Glu Ala Ala Lys Lys Pro Pro Lys Ile Lys
530                 535                 540

His Ala Glu Leu
545

<210> SEQ ID NO 13
<211> LENGTH: 1660
<212> TYPE: DNA
<213> ORGANISM: Unknown
<220> FEATURE:
<223> OTHER INFORMATION: Synthic gene
<220> FEATURE:
<221> NAME/KEY: exon
<222> LOCATION: (7)..(1650)
<223> OTHER INFORMATION: Pig Liver esterase 5
<220> FEATURE:

-continued

```
<221> NAME/KEY: CDS
<222> LOCATION: (7)..(1650)
<223> OTHER INFORMATION: Pig Liver esterase 5

<400> SEQUENCE: 13 catatg gga caa cca gct tcg ccg cct gtc gtt gat acc gct caa gga      48
       Gly Gln Pro Ala Ser Pro Pro Val Val Asp Thr Ala Gln Gly
       1               5                   10 cga gtc ttg ggt aag tac gtc tct tta gag gga ttg gca caa ccg gtt    96
Arg Val Leu Gly Lys Tyr Val Ser Leu Glu Gly Leu Ala Gln Pro Val
15                  20                  25                  30 gct gtc ttc ttg gga gtc cct ttt gct aag cca cct ctt gga tct ttg   144
Ala Val Phe Leu Gly Val Pro Phe Ala Lys Pro Pro Leu Gly Ser Leu
                35                  40                  45 agg ttt gcc ccg ccg caa cca gca gag cca tgg tct ttc gtt aag aac   192
Arg Phe Ala Pro Pro Gln Pro Ala Glu Pro Trp Ser Phe Val Lys Asn
    50                  55                  60 act act tcc tac cct cca atg tgt tgt caa gat cca gtc gca gga caa   240
Thr Thr Ser Tyr Pro Pro Met Cys Cys Gln Asp Pro Val Ala Gly Gln
65                  70                  75 atg acg tca gac cta ttc act aac gga aag gaa agg ctt atc ccg gag   288
Met Thr Ser Asp Leu Phe Thr Asn Gly Lys Glu Arg Leu Ile Pro Glu
        80                  85                  90 ttc tct gag gat tgc ctt tac cta aat att tac act cct gcc gat ttg   336
Phe Ser Glu Asp Cys Leu Tyr Leu Asn Ile Tyr Thr Pro Ala Asp Leu
95                  100                 105                 110 aca aag agg ggt agg ttg ccg gtt atg gtt tgg att cat gga gga ggt   384
Thr Lys Arg Gly Arg Leu Pro Val Met Val Trp Ile His Gly Gly Gly
            115                 120                 125 ttg gtt gtt ggc gga gca tcc act tat gac gga ttg gct ctt gcc gcg   432
Leu Val Val Gly Gly Ala Ser Thr Tyr Asp Gly Leu Ala Leu Ala Ala
        130                 135                 140 cac gag aac gtt gtt gtt gtt gct att caa tac cgt ttg ggt att tgg   480
His Glu Asn Val Val Val Val Ala Ile Gln Tyr Arg Leu Gly Ile Trp
    145                 150                 155 gga ttt ttc tcc aca gga gat gag cat tcc cgt gga aac tgg ggc cat   528
Gly Phe Phe Ser Thr Gly Asp Glu His Ser Arg Gly Asn Trp Gly His
160                 165                 170 tta gat caa gtt gct gca ttg cat tgg gtc caa gaa aac att gct aac   576
Leu Asp Gln Val Ala Ala Leu His Trp Val Gln Glu Asn Ile Ala Asn
175                 180                 185                 190 ttc gga ggt gat cca ggt tct gtt act att ttc gga gaa tca gca ggc   624
Phe Gly Gly Asp Pro Gly Ser Val Thr Ile Phe Gly Glu Ser Ala Gly
            195                 200                 205 gga gag agt gtc tct gta ttg gtt tta tca cca tta gct aag aac ctt   672
Gly Glu Ser Val Ser Val Leu Val Leu Ser Pro Leu Ala Lys Asn Leu
        210                 215                 220 ttt cat cgt gct att tcc gaa agt ggt gtt gct ttt acc gcc ggt ttg   720
Phe His Arg Ala Ile Ser Glu Ser Gly Val Ala Phe Thr Ala Gly Leu
    225                 230                 235 gtc agg aag gat atg aag gcc gca gcc aag cag atc gct gtc ctt gca   768
Val Arg Lys Asp Met Lys Ala Ala Ala Lys Gln Ile Ala Val Leu Ala
240                 245                 250 gga tgc aaa act act act tcg gca gtc ttc gtg cat tgt ttg cgt caa   816
Gly Cys Lys Thr Thr Thr Ser Ala Val Phe Val His Cys Leu Arg Gln
255                 260                 265                 270 aag tcg gaa gat gaa ctt tta gac ctc acg ttg aag atg aaa ttc ttt   864
Lys Ser Glu Asp Glu Leu Leu Asp Leu Thr Leu Lys Met Lys Phe Phe
            275                 280                 285 gcc ctt gac tta cac gga gat cca agg gaa tct cac cct ttt ttg acc   912
```

```
                Ala Leu Asp Leu His Gly Asp Pro Arg Glu Ser His Pro Phe Leu Thr
                            290                 295                 300 act gtt gtt gac gga gtt ttg ttg cct aag atg cct gag gaa atc ttg        960
Thr Val Val Asp Gly Val Leu Leu Pro Lys Met Pro Glu Glu Ile Leu
            305                 310                 315 gcc gag aag gac ttt aac acc gtc cca tac att gtt gga att aac aag       1008
Ala Glu Lys Asp Phe Asn Thr Val Pro Tyr Ile Val Gly Ile Asn Lys
        320                 325                 330 cag gag ttc gga tgg ctt ttg cca acg atg atg gga ttt cct ctt tcc       1056
Gln Glu Phe Gly Trp Leu Leu Pro Thr Met Met Gly Phe Pro Leu Ser
335                 340                 345                 350 gag gga aag ttg gat caa aag acg gct acg tca ctt ttg tgg aag tcc       1104
Glu Gly Lys Leu Asp Gln Lys Thr Ala Thr Ser Leu Leu Trp Lys Ser
                355                 360                 365 tac cca att gcc aac att cct gaa gag ttg acc cca gtt gct acc gat       1152
Tyr Pro Ile Ala Asn Ile Pro Glu Glu Leu Thr Pro Val Ala Thr Asp
            370                 375                 380 aag tat tta gga gga aca gat gat cct gtc aaa aag aaa gat ttg ttt       1200
Lys Tyr Leu Gly Gly Thr Asp Asp Pro Val Lys Lys Lys Asp Leu Phe
        385                 390                 395 ttg gat ctg atg gga gac gtt gtt ttc ggc gtc cca tca gtt acg gtt       1248
Leu Asp Leu Met Gly Asp Val Val Phe Gly Val Pro Ser Val Thr Val
400                 405                 410 gct cgt cag cat agg gac gca gga gct cca act tac atg tat gag ttc       1296
Ala Arg Gln His Arg Asp Ala Gly Ala Pro Thr Tyr Met Tyr Glu Phe
415                 420                 425                 430 caa tat cgt cca tct ttt tca tcg gat aag aaa cct aag acg gtt att       1344
Gln Tyr Arg Pro Ser Phe Ser Ser Asp Lys Lys Pro Lys Thr Val Ile
                435                 440                 445 gga gat cat gga gac gaa att ttt tcc gtc ttc ggc gcc cca ttc ctc       1392
Gly Asp His Gly Asp Glu Ile Phe Ser Val Phe Gly Ala Pro Phe Leu
            450                 455                 460 aga ggt gac gct cca gag gaa gaa gtc agt ctt tct aag acg gtt atg       1440
Arg Gly Asp Ala Pro Glu Glu Glu Val Ser Leu Ser Lys Thr Val Met
        465                 470                 475 aaa ttt tgg gct aac ttc gcc cgt agt gga aac cct aat gga gaa gga       1488
Lys Phe Trp Ala Asn Phe Ala Arg Ser Gly Asn Pro Asn Gly Glu Gly
480                 485                 490 ttg cct cac tgg ccg atg tac gat caa gag gag gga tac ctt caa att       1536
Leu Pro His Trp Pro Met Tyr Asp Gln Glu Glu Gly Tyr Leu Gln Ile
495                 500                 505                 510 ggt gtc aac act caa gca gct aag agg ttg aaa ggc gag gag gtt gct       1584
Gly Val Asn Thr Gln Ala Ala Lys Arg Leu Lys Gly Glu Glu Val Ala
                515                 520                 525 ttt tgg aac gac ctg ttg tcc aag gaa gca gca aag aag cca cct aag       1632
Phe Trp Asn Asp Leu Leu Ser Lys Glu Ala Ala Lys Lys Pro Pro Lys
            530                 535                 540 ata aag cac gcc gaa ttg taataagctt                                    1660
Ile Lys His Ala Glu Leu
        545

<210> SEQ ID NO 14
<211> LENGTH: 548
<212> TYPE: PRT
<213> ORGANISM: Unknown
<220> FEATURE:
<223> OTHER INFORMATION: Synthetic Construct

<400> SEQUENCE: 14

Gly Gln Pro Ala Ser Pro Val Val Asp Thr Ala Gln Gly Arg Val
1               5                   10                  15
```

-continued

Leu Gly Lys Tyr Val Ser Leu Glu Gly Leu Ala Gln Pro Val Ala Val
            20                  25                  30

Phe Leu Gly Val Pro Phe Ala Lys Pro Pro Leu Gly Ser Leu Arg Phe
            35                  40                  45

Ala Pro Pro Gln Pro Ala Glu Pro Trp Ser Phe Val Lys Asn Thr Thr
50                  55                  60

Ser Tyr Pro Pro Met Cys Cys Gln Asp Pro Val Ala Gly Gln Met Thr
65                  70                  75                  80

Ser Asp Leu Phe Thr Asn Gly Lys Glu Arg Leu Ile Pro Glu Phe Ser
                85                  90                  95

Glu Asp Cys Leu Tyr Leu Asn Ile Tyr Thr Pro Ala Asp Leu Thr Lys
                100                 105                 110

Arg Gly Arg Leu Pro Val Met Val Trp Ile His Gly Gly Leu Val
                115                 120                 125

Val Gly Gly Ala Ser Thr Tyr Asp Gly Leu Ala Leu Ala Ala His Glu
            130                 135                 140

Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp
                165                 170                 175

Gln Val Ala Ala Leu His Trp Val Gln Glu Asn Ile Ala Asn Phe Gly
                180                 185                 190

Gly Asp Pro Gly Ser Val Thr Ile Phe Gly Glu Ser Ala Gly Gly Glu
                195                 200                 205

Ser Val Ser Val Leu Val Leu Ser Pro Leu Ala Lys Asn Leu Phe His
            210                 215                 220

Arg Ala Ile Ser Glu Ser Gly Val Ala Phe Thr Ala Gly Leu Val Arg
225                 230                 235                 240

Lys Asp Met Lys Ala Ala Lys Gln Ile Ala Val Leu Ala Gly Cys
                245                 250                 255

Lys Thr Thr Thr Ser Ala Val Phe Val His Cys Leu Arg Gln Lys Ser
                260                 265                 270

Glu Asp Glu Leu Leu Asp Leu Thr Leu Lys Met Lys Phe Phe Ala Leu
            275                 280                 285

Asp Leu His Gly Asp Pro Arg Glu Ser His Pro Phe Leu Thr Thr Val
            290                 295                 300

Val Asp Gly Val Leu Leu Pro Lys Met Pro Glu Glu Ile Leu Ala Glu
305                 310                 315                 320

Lys Asp Phe Asn Thr Val Pro Tyr Ile Val Gly Ile Asn Lys Gln Glu
                325                 330                 335

Phe Gly Trp Leu Leu Pro Thr Met Met Gly Phe Pro Leu Ser Glu Gly
                340                 345                 350

Lys Leu Asp Gln Lys Thr Ala Thr Ser Leu Leu Trp Lys Ser Tyr Pro
            355                 360                 365

Ile Ala Asn Ile Pro Glu Glu Leu Thr Pro Val Ala Thr Asp Lys Tyr
            370                 375                 380

Leu Gly Gly Thr Asp Asp Pro Val Lys Lys Lys Asp Leu Phe Leu Asp
385                 390                 395                 400

Leu Met Gly Asp Val Val Phe Gly Val Pro Ser Val Thr Val Ala Arg
                405                 410                 415

Gln His Arg Asp Ala Gly Ala Pro Thr Tyr Met Tyr Glu Phe Gln Tyr
            420                 425                 430

```
Arg Pro Ser Phe Ser Ser Asp Lys Lys Pro Lys Thr Val Ile Gly Asp
            435                 440                 445

His Gly Asp Glu Ile Phe Ser Val Phe Gly Ala Pro Phe Leu Arg Gly
        450                 455                 460

Asp Ala Pro Glu Glu Val Ser Leu Ser Lys Thr Val Met Lys Phe
465                 470                 475                 480

Trp Ala Asn Phe Ala Arg Ser Gly Asn Pro Asn Gly Glu Gly Leu Pro
                485                 490                 495

His Trp Pro Met Tyr Asp Gln Glu Glu Gly Tyr Leu Gln Ile Gly Val
            500                 505                 510

Asn Thr Gln Ala Ala Lys Arg Leu Lys Gly Glu Glu Val Ala Phe Trp
        515                 520                 525

Asn Asp Leu Leu Ser Lys Glu Ala Ala Lys Lys Pro Pro Lys Ile Lys
530                 535                 540

His Ala Glu Leu
545

<210> SEQ ID NO 15
<211> LENGTH: 41
<212> TYPE: DNA
<213> ORGANISM: Unknown
<220> FEATURE:
<223> OTHER INFORMATION: Primer for L43D F

<400> SEQUENCE: 15
gtcccttttg ctaagccacc tgacggatct ttgaggtttg c                    41

<210> SEQ ID NO 16
<211> LENGTH: 41
<212> TYPE: DNA
<213> ORGANISM: Unknown
<220> FEATURE:
<223> OTHER INFORMATION: Primer for L43D R

<400> SEQUENCE: 16
gcaaacctca agatccgtca ggtggcttag caaaaggga c                     41

<210> SEQ ID NO 17
<211> LENGTH: 37
<212> TYPE: DNA
<213> ORGANISM: Unknown
<220> FEATURE:
<223> OTHER INFORMATION: Primer for T260P F

<400> SEQUENCE: 17
gcaggatgca aaactactcc ttcggcagtc ttcgtgc                         37

<210> SEQ ID NO 18
<211> LENGTH: 37
<212> TYPE: DNA
<213> ORGANISM: Unknown
<220> FEATURE:
<223> OTHER INFORMATION: Primer for T260P R

<400> SEQUENCE: 18
gcacgaagac tgccgaagga gtagttttgc atcctgc                         37

<210> SEQ ID NO 19
<211> LENGTH: 37
<212> TYPE: DNA
<213> ORGANISM: Unknown
<220> FEATURE:
<223> OTHER INFORMATION: Primer for T260A F
```

```
<400> SEQUENCE: 19
gcaggatgca aaactactgc ttcggcagtc ttcgtgc                                    37

<210> SEQ ID NO 20
<211> LENGTH: 37
<212> TYPE: DNA
<213> ORGANISM: Unknown
<220> FEATURE:
<223> OTHER INFORMATION: Primer for T260A R

<400> SEQUENCE: 20
gcacgaagac tgccgaagca gtagttttgc atcctgc                                    37

<210> SEQ ID NO 21
<211> LENGTH: 33
<212> TYPE: DNA
<213> ORGANISM: Unknown
<220> FEATURE:
<223> OTHER INFORMATION: Primer for T263D F

<400> SEQUENCE: 21
ctactacttc ggcagacttc gtgcattgtt tgc                                        33

<210> SEQ ID NO 22
<211> LENGTH: 33
<212> TYPE: DNA
<213> ORGANISM: Unknown
<220> FEATURE:
<223> OTHER INFORMATION: Primer for T263D R

<400> SEQUENCE: 22
gcaaacaatg cacgaagtct gccgaagtag tag                                        33

<210> SEQ ID NO 23
<211> LENGTH: 41
<212> TYPE: DNA
<213> ORGANISM: Unknown
<220> FEATURE:
<223> OTHER INFORMATION: Primer for V263G F

<400> SEQUENCE: 23
caaaactact acttcggcag ggttcgtgca ttgtttgcgt c                               41

<210> SEQ ID NO 24
<211> LENGTH: 41
<212> TYPE: DNA
<213> ORGANISM: Unknown
<220> FEATURE:
<223> OTHER INFORMATION: Primer for V263G R

<400> SEQUENCE: 24
gacgcaaaca atgcacgaac cctgccgaag tagtagtttt g                               41
```

The invention claimed is:

1. An isolated polypeptide having an esterase activity comprising hydrolysis of at least one of (4E)-5-chloro-2-isopropylpent-4-enoic-acid methyl ester, dimethyl-3-(3,4-dichlorphenyl)-glutarate, or para-nitrophenyl acetate, said polypeptide comprising an amino acid sequence shown in any one of SEQ ID NO's 2, 4, 6, 8, 10, 12 or 14 or a homologue thereof, wherein the amino acid sequence or homologue thereof has more than 95% identity to any one of 2, 4, 6, 8, 10, 12 or 14, said amino acid sequence or homologue thereof comprising an amino acid substitution or deletion of one or more amino acids as compared to any one of SEQ ID NO's 2, 4, 6, 8, 10, 12 or 14, wherein the at least one amino acid substitution or deletion has taken place at an amino acid position which is located at a point of interaction of monomers when the monomers are forming multimers and which destroys that point of interaction between the monomers, wherein the substitution or deletion has been carried out at at least one amino acid position corresponding to positions 43, 260 or 263 of SEQ ID NO: 2, and resulting in the polypeptide having an increased concentration of the fraction of the polypeptide being present as an active and soluble protein in cleared lysate of the polypeptide expressed in *E.coli* relative to the concentration of the fraction of the polypeptide without the substitution or deletion being present as an active and soluble protein in cleared lysate of the polypeptide without the at least one substitution or deletion expressed in *E.coli* under the same conditions.

2. An isolated polypeptide according to claim 1, which polypeptide shows an increase of at least 10% in said esterase activity compared to the esterase activity of the corresponding wild-type polypeptide without said deletion or substitution.

3. An isolated polypeptide according to claim 1, wherein the at least one amino acid substitution is selected from the group consisting of substitutions corresponding to L43D, T260P, T260A, V263D, and V263G in SEQ ID NO: 2.

4. An isolated polypeptide according to claim 1, comprising at least one further mutation selected from the group consisting of substitutions corresponding to L238V and F234S in SEQ ID NO: 2.

5. A nucleic acid sequence encoding the polypeptide according to claim 1.

6. In a process of manufacturing acids, esters or alcohols, comprising contacting an ester with an esterase, wherein the improvement comprises hydrolysis of the ester with an isolated polypeptide according to claim 1.

7. In a process according to claim 6, wherein the hydrolysis results in production of at least one of α-alkylated acids and α-alkylated esters.

8. In a process according to claim 7, wherein α-alkylated acids are produced, the process further comprising selecting optically pure α-alkylated acids from the a-alkylated acids, and then reducing said optically pure α-alkylated acids to their corresponding alcohols.

9. In a process according to claim 6, wherein alcohols are manufactured, said alcohols being further processed to manufacture dipeptide mimetics.

10. In a process according to claim 9, wherein the dipeptide mimetics are blood pressure lowering agents.

11. A process of manufacturing acids comprising hydrolyzing at least one ester by contacting the ester with an esterase to produce said acids, wherein the esterase is an isolated polypeptide according to claim 1.

12. A process of manufacturing alcohols comprising hydrolyzing at least one ester by contacting the ester with an esterase to produce an acid and reducing the acid to said alcohol, wherein the esterase is an isolated polypeptide according to claim 1.

13. A process of producing an increased concentration of a desired ester from a mixture of esters containing said desired ester and undesired esters, said process comprising selectively hydrolyzing the undesired ester of said mixture with an isolated polypeptide according to claim 1, so that the desired ester remains.

* * * * *